(12) United States Patent
Nanikashvili et al.

(10) Patent No.: US 8,265,907 B2
(45) Date of Patent: Sep. 11, 2012

(54) SYSTEM AND A METHOD FOR PHYSIOLOGICAL MONITORING

(75) Inventors: Reuven Nanikashvili, Ashdod (IL); Yacov Geva, Rehovot (IL); Nir Geva, Nes Ziona (IL)

(73) Assignee: Card Guard Scientific Survival Ltd., Rehovot (IL)

(*) Notice: Subject to any disclaimer, the term of this patent is extended or adjusted under 35 U.S.C. 154(b) by 298 days.

(21) Appl. No.: 12/468,134

(22) Filed: May 19, 2009

(65) Prior Publication Data

US 2010/0117835 A1    May 13, 2010

Related U.S. Application Data

(63) Continuation-in-part of application No. 11/059,791, filed on Feb. 16, 2005, now Pat. No. 7,542,878, which is a continuation of application No. 10/876,139, filed on Jun. 23, 2004, now abandoned, which is a continuation-in-part of application No. 10/086,633, filed on Mar. 4, 2002, now Pat. No. 7,222,054, which is a continuation-in-part of application No. 09/261,136, filed on Mar. 3, 1999, now Pat. No. 6,366,871.

(51) Int. Cl.
*G06F 19/00* (2011.01)

(52) U.S. Cl. ......................... 702/188; 600/301

(58) Field of Classification Search .................. 702/188, 702/182–185, 117, 118; 600/301
See application file for complete search history.

(56) References Cited

U.S. PATENT DOCUMENTS

| | | |
|---|---|---|
| 3,776,228 A | 12/1973 | Semler |
| 3,779,249 A | 12/1973 | Semler |
| 4,312,358 A | 1/1982 | Barney |
| 4,364,397 A | 12/1982 | Citron et al. |
| 4,367,752 A | 1/1983 | Jimenez et al. |
| 4,531,527 A | 7/1985 | Reinhold |
| 4,572,182 A | 2/1986 | Royse |
| 4,583,553 A | 4/1986 | Shah et al. |
| 4,622,979 A | 11/1986 | Katchis et al. |
| 4,625,730 A | 12/1986 | Fountain et al. |
| 4,803,625 A | 2/1989 | Fu et al. |
| 4,889,131 A | 12/1989 | Salem et al. |

(Continued)

FOREIGN PATENT DOCUMENTS

EP    957964 A1    11/1997

(Continued)

OTHER PUBLICATIONS

Braemar-eCardio's Initial Non-Infringement, Invalidity and Unenforceability; *Lifewatch* v. *Braemar* (IL) Civil Action No. 09-06001; filed Feb. 17, 2010.

(Continued)

*Primary Examiner* — Edward Raymond
(74) *Attorney, Agent, or Firm* — Reches Patents

(57) ABSTRACT

A personal health monitor, including: (a) a physiological data input device operative to gather physiological data; (b) a detachable module that is detachably connected to a multi-purpose personal data accessory, operative to transmit the physiological data to the multi-purpose personal data accessory; and (c) the multi-purpose personal data accessory, whereas the multi-purpose personal data accessory is adapted to execute health monitoring software such as to enable the multi-purpose personal data accessory to receive the physiological data, process the physiological data to provide processed physiological data and control a long range transmission of the processed physiological data to a remote entity.

20 Claims, 14 Drawing Sheets

U.S. PATENT DOCUMENTS

| | | | |
|---|---|---|---|
| 4,920,489 A | 4/1990 | Hubelbank et al. |
| 4,938,228 A | 7/1990 | Righter et al. |
| 4,958,641 A | 9/1990 | Digby et al. |
| 4,967,756 A | 11/1990 | Hewitt |
| 4,977,899 A | 12/1990 | Digby et al. |
| 5,012,814 A | 5/1991 | Mills et al. |
| 5,058,597 A | 10/1991 | Onoda et al. |
| 5,090,418 A | 2/1992 | Squires et al. |
| 5,111,396 A | 5/1992 | Mills et al. |
| 5,128,552 A | 7/1992 | Fang et al. |
| 5,181,519 A | 1/1993 | Bible |
| 5,191,891 A | 3/1993 | Righter |
| 5,201,321 A | 4/1993 | Fulton |
| 5,205,295 A | 4/1993 | Del Mar et al. |
| 5,226,424 A | 7/1993 | Bible |
| 5,226,425 A | 7/1993 | Righter |
| 5,238,001 A | 8/1993 | Gallant et al. |
| D341,659 S | 11/1993 | Homayoun et al. |
| 5,289,824 A | 3/1994 | Mills et al. |
| 5,304,186 A | 4/1994 | Semler et al. |
| 5,313,953 A | 5/1994 | Yomtov et al. |
| 5,317,269 A | 5/1994 | Mills et al. |
| 5,333,616 A | 8/1994 | Mills et al. |
| 5,339,824 A | 8/1994 | Engira |
| 5,343,869 A | 9/1994 | Pross et al. |
| 5,343,870 A | 9/1994 | Gallant et al. |
| 5,348,008 A | 9/1994 | Bornn et al. |
| 5,351,695 A | 10/1994 | Mills et al. |
| 5,365,935 A | 11/1994 | Righter et al. |
| 5,417,222 A | 5/1995 | Dempsey et al. |
| 5,467,773 A | 11/1995 | Bergelson et al. |
| 5,518,001 A | 5/1996 | Snell |
| 5,522,396 A | 6/1996 | Langer et al. |
| D372,785 S | 8/1996 | Sabri et al. |
| 5,544,661 A | 8/1996 | Davis et al. |
| 5,581,369 A | 12/1996 | Righter et al. |
| D377,983 S | 2/1997 | Sabri et al. |
| 5,613,495 A | 3/1997 | Mills et al. |
| 5,634,468 A | 6/1997 | Platt et al. |
| 5,652,570 A | 7/1997 | Lepkofker |
| 5,678,562 A | 10/1997 | Sellers |
| 5,678,571 A * | 10/1997 | Brown ............... 128/898 |
| 5,701,894 A | 12/1997 | Cherry et al. |
| 5,704,364 A | 1/1998 | Saltzstein et al. |
| 5,724,025 A | 3/1998 | Tavori |
| 5,730,143 A | 3/1998 | Schwarzberg |
| 5,735,285 A | 4/1998 | Albert |
| 5,748,103 A | 5/1998 | Flach et al. |
| 5,772,586 A | 6/1998 | Heinonen |
| 5,807,336 A | 9/1998 | Russo et al. |
| 5,827,179 A | 10/1998 | Lichter et al. |
| 5,840,020 A | 11/1998 | Heinonen |
| 5,873,369 A | 2/1999 | Laniado et al. |
| 5,876,351 A | 3/1999 | Rhode |
| 5,877,675 A | 3/1999 | Rebstrock et al. |
| 5,885,245 A | 3/1999 | Lynch et al. |
| 5,895,371 A | 4/1999 | Levitas et al. |
| 5,929,761 A | 7/1999 | Van der Laan et al. |
| 5,941,829 A | 8/1999 | Saltzstein et al. |
| D414,870 S | 10/1999 | Saltzstein et al. |
| 5,976,083 A | 11/1999 | Richardson et al. |
| 6,053,887 A | 4/2000 | Levitas et al. |
| D427,315 S | 6/2000 | Saltzstein et al. |
| 6,072,396 A | 6/2000 | Gaukel et al. |
| 6,083,248 A | 7/2000 | Thompson |
| 6,084,510 A | 7/2000 | Lemelson et al. |
| 6,100,806 A | 8/2000 | Gaukel et al. |
| 6,102,856 A | 8/2000 | Groff et al. |
| 6,135,949 A | 10/2000 | Russo et al. |
| 6,159,147 A | 12/2000 | Lichter et al. |
| 6,173,198 B1 | 1/2001 | Schulze et al. |
| 6,198,394 B1 | 3/2001 | Jacobsen et al. |
| 6,231,560 B1 | 5/2001 | Bui et al. |
| 6,289,238 B1 | 9/2001 | Besson et al. |
| 6,364,834 B1 | 4/2002 | Reuss et al. |
| 6,366,871 B1 | 4/2002 | Geva |
| 6,398,727 B1 | 6/2002 | Bui et al. |
| 6,478,736 B1 | 11/2002 | Mault |
| 6,513,532 B2 | 2/2003 | Mault |
| 6,549,756 B1 | 4/2003 | Engstrom |
| 6,579,231 B1 | 6/2003 | Phipps |
| 6,595,929 B2 | 7/2003 | Stivoric et al. |
| 6,616,613 B1 | 9/2003 | Goodman |
| 6,790,178 B1 | 9/2004 | Mault et al. |
| 6,804,558 B2 | 10/2004 | Haller et al. |
| 6,871,089 B2 | 3/2005 | Korzinov et al. |
| 6,893,396 B2 | 5/2005 | Schulze et al. |
| 7,009,511 B2 | 3/2006 | Mazar et al. |
| 7,108,659 B2 | 9/2006 | Ross et al. |
| 7,188,151 B2 | 3/2007 | Kumar et al. |
| 7,215,991 B2 | 5/2007 | Besson et al. |
| 7,222,054 B2 | 5/2007 | Geva |
| 7,257,448 B2 | 8/2007 | Crowe et al. |
| 7,299,159 B2 | 11/2007 | Nanikashvili |
| 7,542,878 B2 | 6/2009 | Nanikashvili |
| 7,596,405 B2 | 9/2009 | Kurzweil et al. |
| 2001/0027384 A1 | 10/2001 | Schulze |
| 2002/0032386 A1 | 3/2002 | Sackner et al. |
| 2002/0032387 A1 | 3/2002 | Geva et al. |
| 2003/0028442 A1 | 2/2003 | Wagstaff et al. |
| 2003/0107487 A1 | 6/2003 | Korman et al. |
| 2003/0149344 A1 | 8/2003 | Nizan |
| 2004/0059205 A1 | 3/2004 | Carlson et al. |
| 2004/0143403 A1 | 7/2004 | Brandon et al. |
| 2004/0225199 A1 | 11/2004 | Evanyk et al. |
| 2004/0266480 A1 | 12/2004 | Hjelt et al. |
| 2005/0124864 A1 | 6/2005 | Mack et al. |

FOREIGN PATENT DOCUMENTS

| | | |
|---|---|---|
| EP | 1181888 | 2/2002 |
| EP | 1238633 | 9/2002 |
| EP | 1782229 | 8/2009 |
| GB | 2372114 A | 8/2002 |
| WO | WO9944494 | 9/1999 |
| WO | WO 01/47597 | 7/2001 |
| WO | WO 02/80762 A1 | 10/2002 |
| WO | WO03075118 | 9/2003 |
| WO | WO2006021956 | 3/2006 |
| WO | WO 2006/001005 A2 | 5/2006 |
| WO | WO2007/083315 | 7/2007 |

OTHER PUBLICATIONS

Braemar-eCardio's Exhibits C-O to Disclosure; *Lifewatch* v. *Braemar* (IL) Civil Action No. 09-06001; filed Feb. 17, 2010.

Mednet's Initial Non-infringement, Invalidity and Unenforceability: *Lifewatch* v. *Braemar* (IL) Civil Action No. 09-06001; filed Feb. 17, 2010.

Mednet's Exhibit D—Initial Invalidity Contentions; *Lifewatch* v. *Braemar* (IL) Civil Action No. 09-06001; filed Feb. 17, 2010.

LW's Responses to Braemar & eCerdio's Initial Invalidity Contentions; *Lifewatch* v. *Braemar* (IL) Civil Action No. 09- 06001; filed Mar. 3, 2010.

LW's Exhibits 1-13 to its Responses to Braemar & eCardio's Initial Invalidity Contentions; *Lifewatch* v. *Braemar* (IL) Civil Action No. 09-06001; filed Mar. 3, 2010.

LW's Responses to Mednet's Initial Invalidity Contentions; *Lifewatch* v. *Braemar* (IL) Civil Action No. 09-06001; filed Mar. 3, 2010.

LW's Exhibits 10-20 to its Responses to Mednet's Initial Invalidity Contentions; *Lifewatch* v. *Braemar* (IL) Civil Action No. 09-06001; filed Mar. 3, 2010.

037.00—Defendants' Opposition to LifeWatch's Motion for PI; *Lifewatch* v. *Medicomp* (FL) 09-CV-01909-Orl-31DAB; filed Dec. 16, 2009.

040.00—Declaration of Shatzer in Opp to Mtn for PI; *Lifewatch* v. *Medicomp* (FL) 09-CV-01909-Orl-31DAB; filed Dec. 16, 2009.

040.18—Exhibit 11; *Lifewatch* v. *Medicomp* (FL) 09-CV-01909-Orl-31DAB; filed Dec. 16, 2009.

040.20—Exhibit 13; *Lifewatch* v. *Medicomp* (FL) 09-CV-01909-Orl-31DAB; filed Dec. 16, 2009.

046.02—Shatzer Amended Exhibit 15; *Lifewatch* v. *Medicomp* (FL) 09-CV-01909-Orl-31DAB; filed Jan. 6, 2010.

040.24—Exhibit 17; *Lifewatch v. Medicomp* (FL) 09-CV-01909-Orl-31DAB; filed Dec. 16, 2009.
040.25—Exhibit 18; *Lifewatch v. Medicomp* (FL) 09-CV-01909-Orl-31DAB; filed Dec. 16, 2009.
040.26—Exhibit 19; *Lifewatch v. Medicomp* (FL) 09-CV-01909-0rl-31DAB; filed Dec. 16, 2009.
040.28—Exhibit 21; *Lifewatch v. Medicomp* (FL) 09-CV-01909-Orl-31DAB; filed Dec. 16, 2009.
040.34—Exhibit 27; *Lifewatch v. Medicomp* (FL) 09-CV-01909-Orl-31DAB; filed Dec. 16, 2009.
040.36—Exhibit 29; *Lifewatch v. Medicomp* (FL) 09-CV-01909-Orl-31DAB; filed Dec. 16, 2009.
053.00—Reply Brief Supporting Motion for Preliminary Injunction; *Lifewatch v. Medicomp* (FL) 09-CV-01909-Orl-31DAB; filed Jan. 15, 2010.
064.00—Medicomp's Demonstrative Presentation as Presented at 1.28.10 Evidentiary Hearing; *Lifewatch v. Medicomp* (FL) 09-CV-01909-Orl-31DAB; filed Jan. 28, 2010.
064.01—pp. 21-40; *Lifewatch v. Medicomp* (FL) 09-CV-01909-Orl-31DAB; filed Jan. 28, 2010.
064.02—pp. 41-60; *Lifewatch v. Medicomp* (FL) 09-CV-01909-Orl-31DAB; filed Jan. 28, 2010.
064.03—pp. 61-80; *Lifewatch v. Medicomp* (FL) 09-CV-01909-Orl-31DAB; filed Jan. 28, 2010.
064.04—pp. 81-100; *Lifewatch v. Medicomp* (FL) 09-CV-01909-Orl-31DAB; filed Jan. 28, 2010.
064.05—pp. 101-119; *Lifewatch v. Medicomp* (FL) 09-CV-01909-Orl-31DAB; filed Jan. 28, 2010.
068.00—Plaintiff's Demonstrative; *Lifewatch v. Medicomp* (FL) 09-CV-01909-Orl-31DAB; filed Jan. 28, 2010.
070.00—Defendants' Response to Plaintiffs' Proposal in Connection with PI & Scheduling; *Lifewatch v. Medicomp* (FL) 09-CV-01909-Orl-31DAB; filed Feb. 2, 2010.
071.00 Order Denying Motion for Preliminary Injunction; *Lifewatch v. Medicomp* (FL) 09-CV-01909-Orl-31DAB; filed Feb. 10, 2010.
081.00—Order granting in part [75] Motion to Stay; *Lifewatch v. Medicomp* (FL) 09-CV-01909-Orl-31DAB; filed Mar. 16, 2010.
WO 06/001005 A3 International Search Report, International Preliminary Report on Patentability and Written Opinion of the International Searching Authority mailed Jun. 29, 2006, for International Patent Application No. PCT/IL2005/000664.
Gomez, "A telemedicine distributed decision-Support System for Diabetes Management," IEEE, Oct. 29, 1992, pp. 1238-1239, USA.
Wiesspeiner & Wu, "Multichannel Ambulatory Monitoring of Circulation Related Biosignals," IEEE, Sep. 23, 1991, pp. 457-460, USA.
Author unknown, "ActiveECG Manual," date unknown, pp. 1-56, location published unknown. (ActiveECG system may have been offered for sale at least since 2001).
Biosensor Corp., "Full Disclosure, Scanning and More!" (brochure for Uniday system), date unknown, printed in USA. (Uniday system may have been offered for sale at least as early as 1987).
Biosensor Corp., "Multiday Interactive Monitoring," (brochure for Multiday system), date unknown, printed in USA. (Multiday system may have been offered for sale at least as early as 1987).
Sony Corp., "Operating Instructions, Sony Clie Personal Entertainment Organizer PEG-NX70V, PEG NX60," 2002, pp. I-100, location published unknown.
EP Patent Application No. 99906437.1, International Search Report dated Aug. 30, 1999.
EP Patent Application No. 99906437.1, Amendment & Substitute Drawing dated Nov. 11, 1999.
EP Patent Application No. 03743496.6, International Search Report dated Dec. 31, 2003.
EP Patent Application No. 03743496.6. Amendment dated Sep. 27, 2004.
EP Patent Application No. 03743496.6, Supplementary European Search Report dated Apr. 3, 2009.
EP Patent Application No. 03743496.6, Communication from Examining Division dated Oct. 14, 2009.
EP Patent Application No. 03743496.6, Reply to Communication from Examining Division dated Apr. 19, 2010.
EP Patent Application No. 05774734.7, International Search Report dated May 26, 2006.
EP Patent Application No. 05774734.7, International Preliminary Report on Patentability dated Mar. 12, 2007.
EP Patent Application No. 05774734.7, Supplementaty European Search Report dated Aug. 27, 2009.
EP Patent Application No. 05774734.7, European Search Opinion dated Aug. 27, 2009.
EP Patent Application No. 05774734.7, Reply to Communication from Examining Division dated Apr. 21, 2010.
EP Patent Application No. 05754578.2, International Search Report dated Aug. 24, 2006.
EP Patent Application No. 05754578.2, International Preliminary Report on Patentability dated Jan. 15, 2007.
EP Patent Application No. 05754578.2, Supplementary European Search Report dated Feb. 18, 2009.
EP Patent Application No. 05754578.2, Communication from Examining Division dated Aug. 4, 2009.
EP Patent Application No. 05754578.2, Reply to Communication from Examining Division dated Feb. 4, 2010.
Sony, "Operating Instructions, Sony Clie Personal Entertainment Organizer PEG-NX70V, PEG NX60," 2002, pp. 1-100.
Braemar-eCardio's Exhibits P-R to Disclosure; *Lifewatch v. Braemar* (IL) Civil Action No. 09-06001; filed Feb. 17, 2010.
Mednet's Initial non-infringement, invalidity and unenforceability; *Lifewatch v. Braemar* (IL) Civil Action No. 09-06001; filed Feb. 17, 2010.
Exhibit C—Mednet's Initial Invalidity Contentions; *Lifewatch v. Braemar* (IL) Civil Action No. 09-06001; filed Feb. 17, 2010.
Braemar and eCardios Amended JointDisc of Init Invalidity Cont Concerning 143 Patent; *Lifewatch v. Braemar* (IL) Civil Action No. 09-06001; filed Feb. 23, 2010.
LW's Responses to Braemar & eCardio's Initial Invalidity Contentions; *Lifewatch v. Braemar* (IL) Civil Action No. 09-06001; filed Mar. 3, 2010.
LW's Exhibits 14-16 to its Responses to Braemar & eCardio's Initial Invalidity Contentions; *Lifewatch v. Braemar* (IL) Civil Action No. 09-06001; filed Mar. 3, 2010.
LW's Exhibits 1-9 to its Responses to Mednet's Initial Invalidity Contentions; *Lifewatch v. Braemar* (IL) Civil Action No. 09-06001; filed Mar. 3, 2010.
Joint Disclosure of Final Invalidity and Unenforceability Contentions; *Lifewatch v. Braemar* (IL) Civil Action No. 09-06001; filed Jun. 23, 2010.
Exhibits to Final Invalidiity and Unenforceability Contentions; *Lifewatch v. Braemar* (IL) Civil Action No. 09-06001; filed Jun. 23, 2010.
065.00—Motion for SI by Braemar and e-Cardio; *Lifewatch v. Braemar* (IL) Civil Action No. 09-06001; filed Jul. 1, 2010.
065.01—Defendants' Memo ISO Motion for Summary Judgment; *Lifewatch v. Braemar* (IL) Civil Action No. 09-06001; filed Jul. 1, 2010.
065.02—Defendants' Statement of Undisputed Material Facts; *Lifewatch v. Braemar* (IL) Civil Action No. 09-06001; filed Jul. 1, 2010.
065.03—Affidavit of Robert D. Jordan; *Lifewatch v. Braemar* (IL) Civil Action No. 09-06001; filed Jul. 1, 2010.
065.04—Affidavit at Matthew Otto; *Lifewatch v. Braemar* (IL) Civil Action No. 09-06001; filed Jul. 1, 2010.
065.05—Affidavit of Paul Brinda; *Lifewatch v. Braemar* (IL) Civil Action No. 09-06001; filed Jul. 1, 2010.
Answer and Counterclaims of Defendants Medicomp, Inc. and United Therapeutics Corporation, Dec. 16, 2009, 10 pgs.
Plaintiff Lifewatch Services, Inc. and Card Guard Scientific Survival, Ltd.'s Answer and Affirmative Defenses to Defandant's Medicomp, Inc. and United Therapeutics Corporation's Counterclaims, Jan. 11, 2010, 9pgs.
Declaration of Oren Reches, Jan. 24, 2010, 2 pgs.
International search report of patent application PCT/IB11/52615 mailed on Nov. 23, 2011.

* cited by examiner

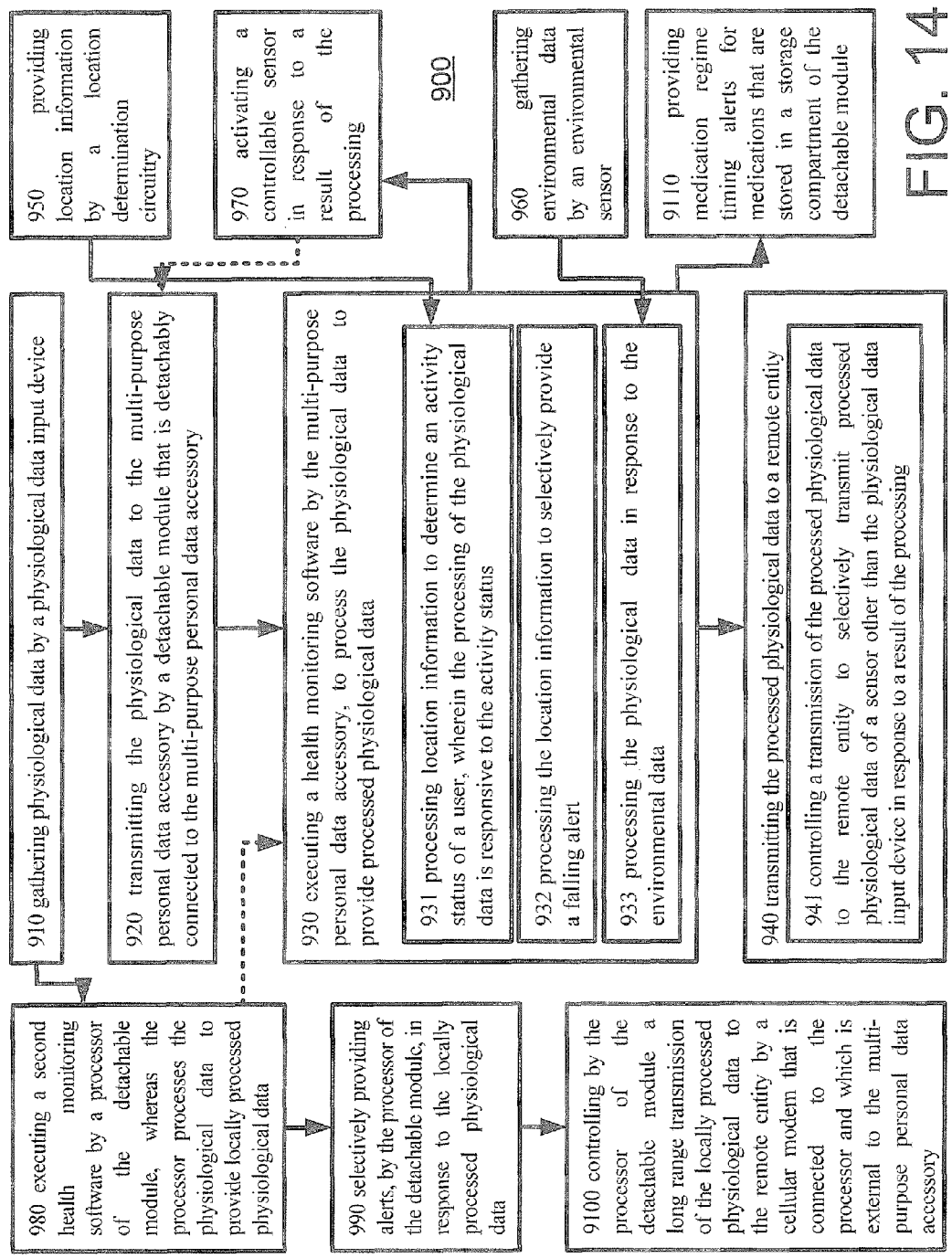

SYSTEM AND A METHOD FOR PHYSIOLOGICAL MONITORING

CROSS REFERENCE TO RELATE APPLICATIONS

This application is a continuation-in-part of U.S. application Ser. No. 11/059,791, filed on Feb. 16, 2005 now U.S. Pat. No. 7,542,878 (and which is entitled "Personal Health Monitor and a Method for Health Monitoring"), which is a continuation of U.S. application Ser. No. 10/876,139, filed on Jun. 23, 2004, now abandoned which is a continuation-in-part of U.S. application Ser. No. 10/086,633, filed on Mar. 4, 2002, now U.S. Pat. No. 7,222,054 which is a continuation-in-part of U.S. application Ser. No. 09/261,136, filed on Mar. 3, 1999, now U.S. Pat. No. 6,366,871 all of which are incorporated herein by reference in their entirety.

FIELD OF THE INVENTION

The invention relates to personal health monitors and methods for health monitoring and especially to a personal health monitor that includes a cellular phone, hand-held device, or other personal data assistant.

BACKGROUND OF THE INVENTION

The amount of hand-Held devices and personal data accessories, such as cellular phones, PDA etc. has dramatically increased during the last two decades. Multiple vendors across the globe invest increasing amounts of research and development efforts to provide highly sophisticated, highly complex cellular phones. The data processing power, Graphical User Interface (GUI) capabilities and computational power of cellular phones dramatically increased during the last decade, as well as the amount of various applications that are supported by modern cellular phones.

Modern cellular phones are adapted to support multimedia applications, data related applications, as well as various games. There are various manners to download software that is later executed by the cellular phone. There are various operating systems that are supported by cellular phones (Such as: Symbian, Linux, BREW, REX, RTX, PALM, PPC2003 etc.). By utilizing cross-operating system software tools, such as the JAVA software suit, applications can be developed almost regardless of the operation systems.

Cellular phone vendors have also dramatically decreased the power consumption of their cellular phones, while increasing the efficiency of cellular phone batteries, thus allowing cellular phones to operate for prolonged periods, before recharging the cellular phone battery. Nevertheless, cellular phones are periodically recharged.

FIG. 1 illustrates a prior art cellular phone 100 that includes a power connector 50 (also referred to as battery connector) for enabling an external device to charge the battery of the cellular phone, an antenna connector 52 (for connecting the cellular phone to an external antenna, such as a car mounted antenna), as well as an additional connector 56 (also referred to as system connector) for connecting the cellular phone to external devices such as audio amplifiers, hands free kit, external memory devices, communication link (RS232, USB and etc.), special data communication link, and the like. The connectors 50, 52 and 56 could be combined in one or two connectors. Other prior art cellular phones, such as some Nokia™ cellular phones, include a system connector and a battery connector. U.S. Pat. No. 6,424,842 of Winstead titled "Dual function connector for cellular phones", which is incorporated herein by reference, provides a complex dual function connector that includes multiple contacts and slots.

FIG. 2 illustrates a prior art cellular phone 100. Cellular phone 100 includes an internal or external antenna 2, RF module 4, base-band processor 6, processor 8, display 10, microphone 12, speakerphone 14, loud speakers 16, analog voice and audio mixer 18, earphones 19, digital to analog converter (DAC) 20, memory module 22, integrated camera 24, USB interface 26, external memory interface 28 and keypad and joystick module 40, Optional Wireless link interface (such as: Bluetooth, WLAN, UWB (Ultra Wide Band) or other wireless link).

The internal antenna 2 can be bypassed by an external antenna 102 that is connected to cellular phone 120 via an antenna connector 54. The power supply 108 is connected on one hand to power connector 50 for recharging battery 21 and is also connected to system connector 56 to provide power from the battery 21.

Cellular phone 100 is capable of: (i) receiving RF signals from antenna 2 or external antenna 102, and vice verse; (ii) receiving audio signals from microphone 12 or an external microphone that may be a part of a hands-free/car-kit assembly; (iii) providing audio signals to loud speakers 16 or to external loud speakers; (iv) receiving information signals such as data and/or video signals from an internal camera 24, or external devices such as an external camera a computer or other cellular phone. Serial Interface, Data link interface or USB interface 26 and external memory interface 28 may receive signals via system connector 56.

Antenna 2 or external antenna 102 receives and transmits Radio Frequency (RF) signals that are provided by or received from Radio Frequency (RF) module 4. RF module 4 is connected between antenna 2 and base-band processor 6 and is able to convert RF signals to base-band signals and vice versa. Base-band processor 6, display 10, and keypad and joystick module 40, as well as integrated camera 24, USB interface 26, external memory interface 28 and digital to analog converter (DAC) 20 are controlled by and connected to processor 8 that may execute various applications. Processor 8 is controlled by a software package that may include an operating system as well as many application software, including Java engines. The software package, as well as various information are stored at memory module 22 that may include RAM as well as ROM memory cells. Memory module 22 is connected to DAC 20 and processor 8. The software package includes at least one software that is related to the transmission of information between the cellular phone and a remote station. This software is also referred to as communication related software.

Cellular phone 100 is able to receive, process and generate audio signals, by DAC 20 and base-band processor 6 that are connected to analog voice and audio mixer 18 that in turn is connected to speakerphone 14, loud speakers 16 and earphones 19. Base-band processor 6 is further connected to microphone 12. Keypad and joystick module 40 includes a multi-way Joystick and multiple keys and soft keys, positioned below display 10.

Cellular phone 100 also includes a short-range module 5, illustrated as being connected to base-band processor 6, for short-range wireless transmission and reception of information. This short-range wireless transmission and reception can be according to various standards, including the Bluetooth, WLAN, ZigB, Wi-Fi, WLAN, UWB and other standards. It is noted that module 5 can be connected to other components of the cellular phone 100. U.S. patent application 2004/0027244 of Menard, titled "Personal medical device communication system and method", which is incorporated herein by reference, provides a description of some prior art short-range and long-range transmission methods that are known in the art.

The following U.S. patent applications, that are incorporated herein by reference, describe cellular phones that are capable of applying short-range transmission: U.S. patent application 2003/0114106 of Miyatsu et al., titled "Mobile internet solution using Java application combined with local wireless interface"; U.S. patent application 2003/0045235 of Mooney et al., titled "Smart Bluetooth interface gateway to mate a non-Bluetooth wireless device with a Bluetooth headset"; and U.S. patent application 2003/0235186 of Park titled "Internet cordless phone".

U.S. patent application 2003/0114106 of Miyatsu et al. describes a telecommunications system and method for downloading application software to a local communications network via an external communications network. The local communications network comprises a plurality of devices including an interface device. The interface device includes an interface for interfacing with the external communications network for downloading an application software from an application software source to the interface device via the external communications network. The local communications network preferably comprises a local wireless network, such as a Bluetooth and wireless networks, and the external communications network preferably comprises a mobile communications network for downloading application software to a mobile phone of the local wireless network A cellular phone that does not include a short-range transceiver, such as a Bluetooth transceiver can be connected to an adapter or other means that facilitates short-range communication with the phone. U.S. patent application 2003/0045235 of Mooney et al. describes a smart Bluetooth interface gateway device that allows a Bluetooth headset to establish an audio connection and communicate with a conventional wireless phone (e.g., a wireless phone that does not have Bluetooth installed). The connection is controlled merely by monitoring the presence of sound and tones in the audio stream from an analog audio jack of a conventional wireless phone. The smart Bluetooth interface gateway device is attached to the wireless phone just as a wired headset would. Use of the wireless phone is the same as if a wired headset were plugged in.

Various methods and devices for monitoring the health of a person are known in the art. They include special hardware for gathering and processing physiological data and a wireless device utilizes for transmitting the gathered information. The special hardware is much less sophisticated and less efficient as the hardware of cellular phones. The development of dedicated hardware is usually costly.

The following U.S. patents and patent applications, are incorporated herein by reference, provide a brief review of state of the art systems and devices: U.S. patent application 2004/0027244 of Menard, titled "Personal medical device communication system and method"; U.S. Pat. No. 5,390,238 of Kirk, et al., titled "Health support system"; U.S. Pat. No. 5,566,676 of Rosenfeldt et al., titled "Pressure data acquisition device for a patient monitoring system"; U.S. Pat. No. 5,772,586 of Heinonen et al., titled "Method for monitoring the health of a patient", U.S. Pat. No. 5,840,020 of Heinonen et al, titled "monitoring method and a monitoring equipment" and U.S. Pat. No. 5,983,193 of Heinonen et al., titled "patient's nursing apparatus and nursing system".

U.S. Pat. No. 6,366,871 titled "Personal ambulatory cellular health monitor for mobile patient" of Geva, which incorporated herein by reference describes an ambulatory patient monitoring apparatus including a portable housing including at least one physiological data input device operative to gather physiological data of the patient, location determination circuitry operative to determine geographic location information of the patient, cellular telephone communications circuitry for communicating the physiological data and the geographic location information to a central health monitoring station, voice communications circuitry. The patient conducts voice communications with a clinician at the central health monitoring station, digital signal processing circuitry for processing signals associated with any of the physiological data input device, the location determination circuitry, the cellular telephone communications circuitry, and the voice communications circuitry, and control circuitry for controlling any of the digital signal processing circuitry, the physiological data input device, the location determination circuitry, the cellular telephone communications circuitry, and the voice communications circuitry.

here is a need to provide an efficient method for health monitoring as well as an efficient personal health monitor.

SUMMARY OF THE INVENTION

A personal health monitor, including: (a) a physiological data input device operative to gather physiological data; (b) a detachable module that is detachably connected to a multi-purpose personal data accessory, operative to transmit the physiological data to the multi-purpose personal data accessory; and (c) the multi-purpose personal data accessory, whereas the multi-purpose personal data accessory is adapted to execute health monitoring software such as to enable the multi-purpose personal data accessory to receive the physiological data, process the physiological data to provide processed physiological data and control a long range transmission of the processed physiological data to a remote entity.

A method for health monitoring, including: (a) gathering physiological data by a physiological data input device; (b) transmitting the physiological data to the multi-purpose personal data accessory by a detachable module that is detachably connected to the multi-purpose personal data accessory; (c) executing health monitoring software by the multi-purpose personal data accessory, to process the physiological data to provide processed physiological data; and (d) transmitting the processed physiological data to a remote entity.

BRIEF DESCRIPTION OF THE DRAWINGS

The subject matter regarded as the invention is particularly pointed out and distinctly claimed in the concluding portion of the specification. The invention, however, both as to organization and method of operation, together with objects, features, and advantages thereof, may best be understood by reference to the following detailed description when read with the accompanying drawings in which:

FIG. 8 illustrates a plug-in unit, according to an embodiment of the invention;

FIG. 14 illustrates a method for health monitoring, according to an embodiment of the invention.

Figure 1:
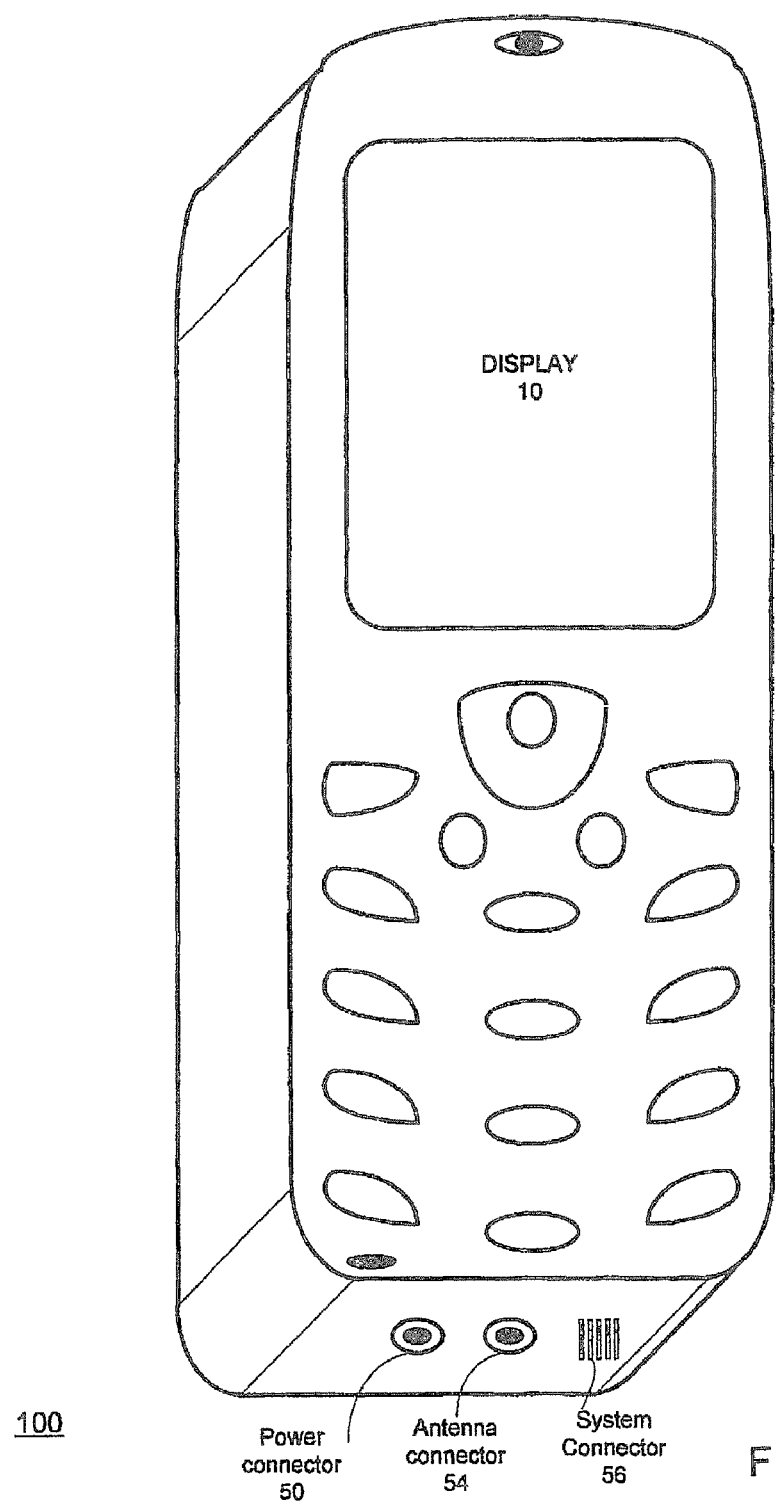
FIGS. 1-2 are schematic diagrams of a prior art cellular phone.

It will be appreciated that for simplicity and clarity of illustration, elements shown in the figures have not necessarily been drawn to scale. For example, the dimensions of some of the elements may be exaggerated relative to other elements for clarity. Further, where considered appropriate, reference numerals may be repeated among the figures to indicate corresponding or analogous elements.

DETAILED DESCRIPTION OF THE PRESENT INVENTION

In the following detailed description, numerous specific details are set forth in order to provide a thorough understanding of the invention. However, it will be understood by those skilled in the art that the present invention may be practiced without these specific details. In other instances, well-known methods, procedures, and components have not been described in detail so as not to obscure the present invention.

The following description mainly refers to monitoring a health of a person. It is noted that this method and monitors can be applied to track multiple persons simultaneously, such as tracking the performances of a team of players.

The following description also refers to a cellular phone that can be provided with health monitoring software that enables the cellular phone to process physiological data, and especially without any addition of complex hardware, such as additional processors. It is noted that the invention can be applied to other multi-task and/or multi-purpose accessories, especially personal data accessories (PDAs) other that cellular phones that in turn may include palm-computers and the like.

The following description describes various transmitters, such as short-range transmitters and long-range transmitters. Each transmitter is associated with a corresponding receiver, but for simplicity of explanation a larger emphasis was placed upon the transmitters.

It is noted that according to various embodiments of the invention the cellular phone (or other personal data accessory) can include a short-range transmitted for transmitting information (such as instructions) to various components (such as physiological data input devices, adapters and the like) that are equipped with corresponding short-range receivers.

Figure 2:
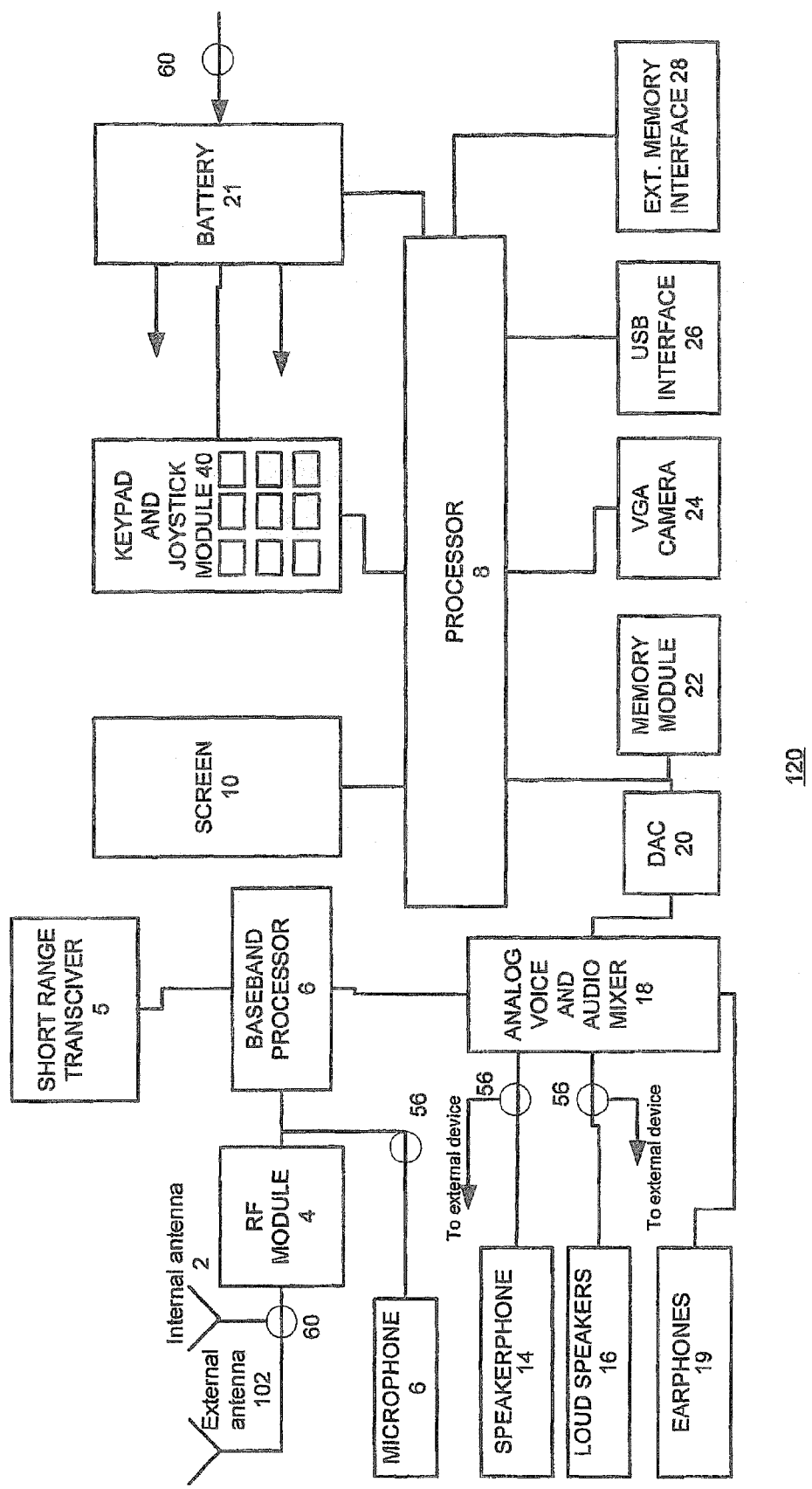

The cellular phone that is referred to in the following figures can resemble the prior art cellular phone 100 of FIGS. 1 and 2 but in addition has health monitoring software for processing physiological data.

FIGS. 3-6 are schematic illustrations of a personal health monitor 1 that includes one or more physiological data input devices and a cellular phone (or another PDA), according to various embodiment of the invention. Each figure illustrates one or more physiological data input devices that may include at least one of the following devices: an electrocardiograph (ECG) input device, a device for monitoring blood oxygen saturation, a device for monitoring respiration, a device for monitoring blood glucose, a device for monitoring blood pressure, a device for monitoring lung function, a device for monitoring Sp02 saturation, a device for monitoring temperature, a device for fat analysis, a drug dispenser, drug taking reminder, a container device, a fetal hart rate monitor device for pregnancy women, EEG device and the like.

Each physiological data input device includes at least one sensor and may also include an analog component such as an analog amplifier, an analog comparator and the like. Such a physiological data input device may also include an analog to digital converter (ADC), although such an ADC is typically located within another component that is connected to the physiological data input device.

Figure 3:
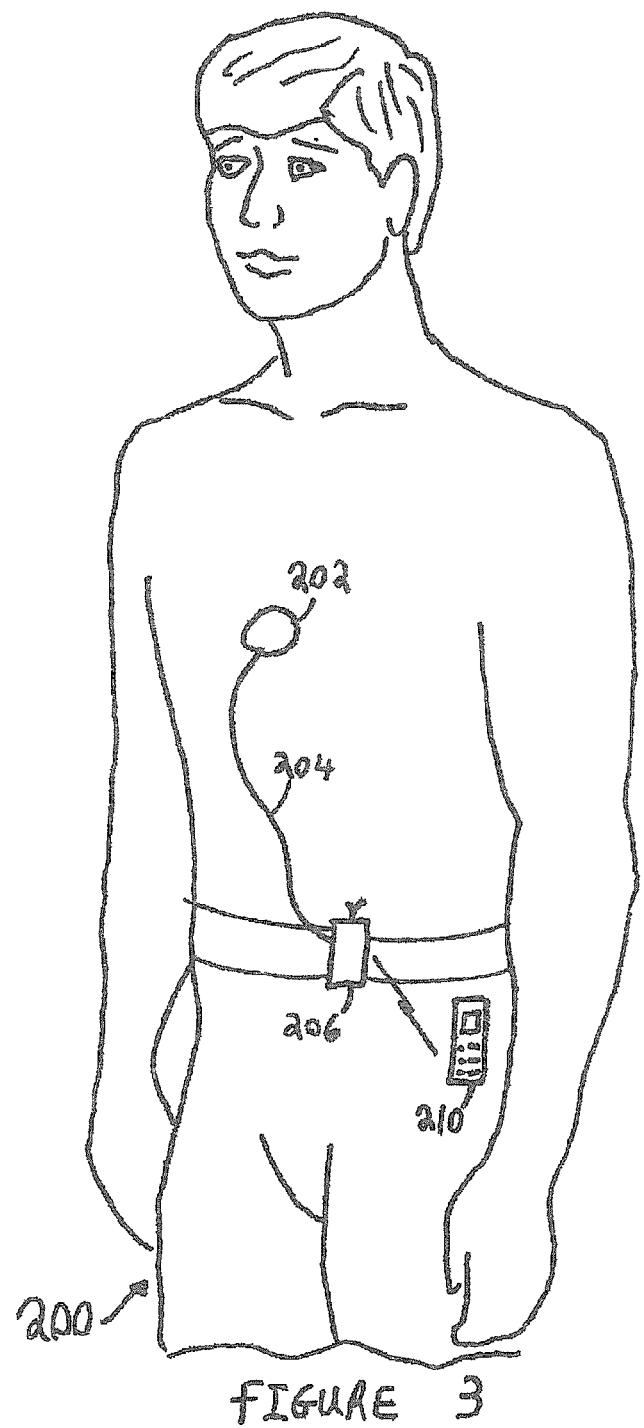
FIGS. 3-6 and 8 are schematic illustrations of a person that is wearing single or multiple physiological data input devices and also carries a cellular phone or PDA, according to an embodiment of the invention.

FIG. 3 illustrates a person 200 that is wearing a physiological data input device 202 operative to gather physiological data, according to an embodiment of the invention. In this figure the physiological data input devices 202 are connected to person 200 by a sticker, but this is not necessarily so. The physiological input device 202 can be connected to an elastic stripe or some type of belt that in turn is worn by person 200.

The physiological data input device 202 is connected by wire 204 to a short-range transmitter 206 or the device 202 is embedded in the short-range transmitter 206. The short-range transmitter 206 is adapted to wirelessly transmit the gathered physiological data to cellular phone 210 or other personal data accessory. Either the physiological data input device 202 or the short-range transmitter 206 include a analog to digital converter for providing a digital stream of signals representative of the physiological condition of the person 200.

According to various embodiments of the invention the short-range transmitter 206 transmits the physiological data to the cellular phone 210 in bursts. Burst transmitters are known in the art and do not require additional explanation. Typically, such a transmitter includes one or more buffers or other memory components (such as a stack, multiple memory cells and the like), for storing data before being transmitted in bursts. The bursts can be transmitted whenever a certain transmission condition is fulfilled (for example—the one or more buffers are full), or in a predefined manner. The burst rate is usually responsive to a ratio between the sampling-rate of the physiological data provided by the physiological data input device and between the transmission bit-rate. Typically the sampling-rate is at selected such as to fulfill the Nyquist condition.

The short-range transmitter 206 can apply error corrections algorithms, such as CRC, in order to compensate for possible errors in the short-range transmission. The short-range transmission can be implemented in a standard manner, for example according to the Bluetooth standard, but this is not necessarily so.

Figure 5:
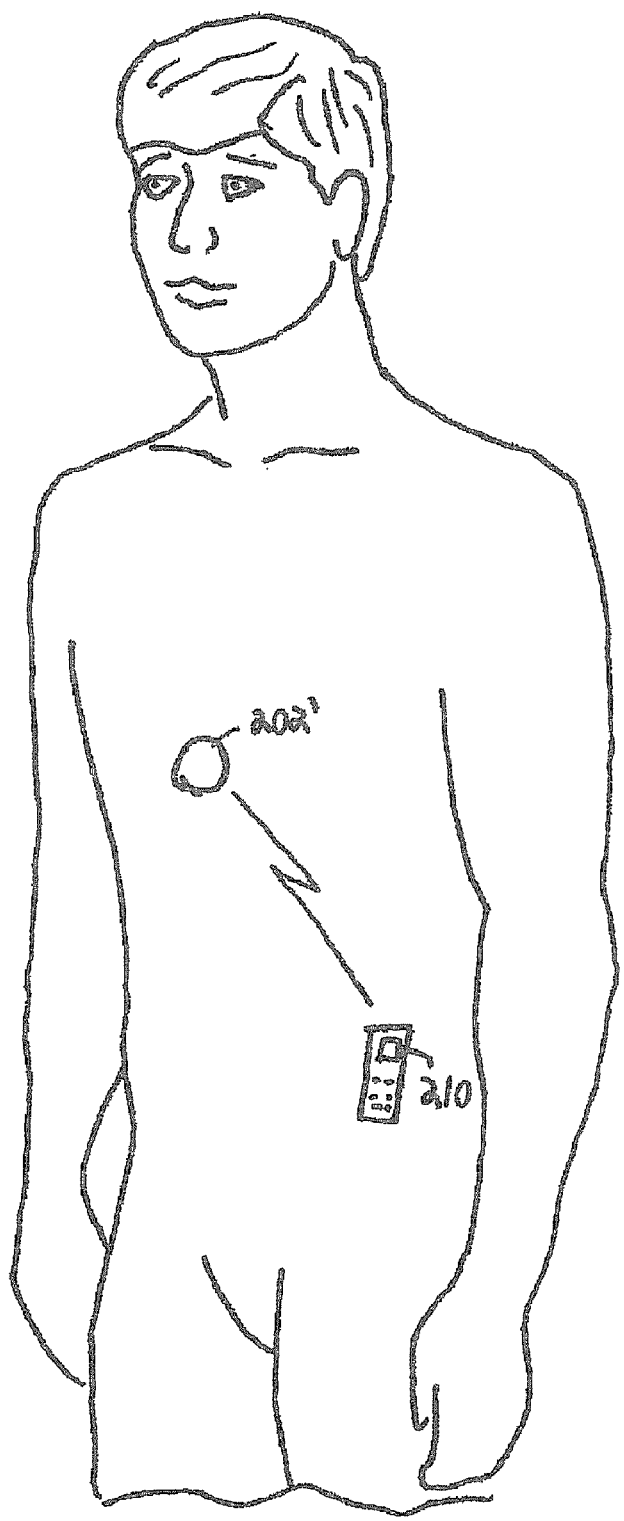

It is further noted that a short-range transmission circuitry can reside within the cellular phone 210 or be attached to the phone by means of a short-range transmission adapter 222, as illustrated in FIG. 5.

Figure 4:
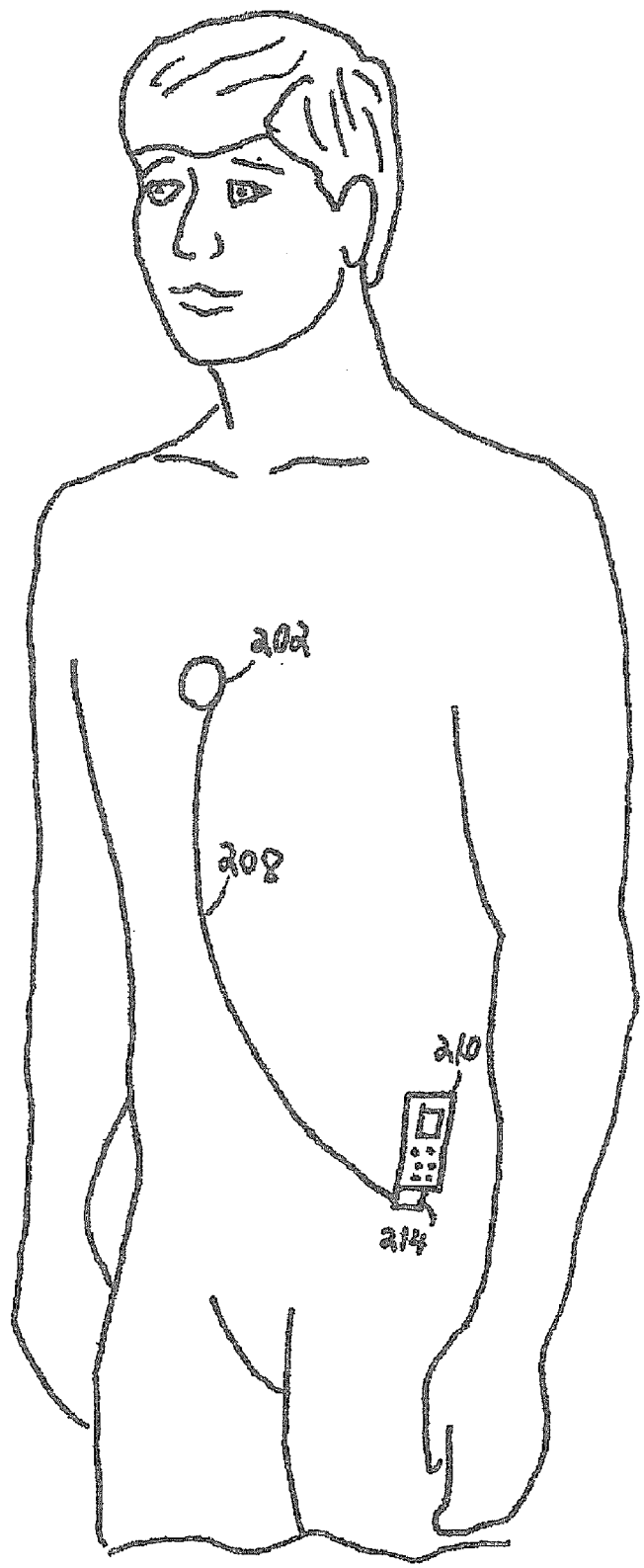

FIG. 4 illustrates another embodiment of the invention in which the physiological data input device 202 is connected via wire 208 to the cellular phone 210 via an additional component, such as protocol adapter 212. The additional component can include a signal converter, adapted to convert signals arriving from the physiological data input device 202 to a format that is recognized by the mobile phone 210. The converter may include an analog to digital converter, communication protocol adapted and the like.

FIG. 5 illustrates another embodiment of the invention in which the physiological data input devices 202' have wireless short-range transmission capabilities and are capable of short-range communication with the cellular phone 210. Electrodes that include wireless transmission capabilities are known in the art and are described, for example, at U.S. Pat. No. 6,577,893 of Besson et al., titled "wireless medical diagnosis and monitoring equipment" which is incorporated herein by reference.

Figure 6:
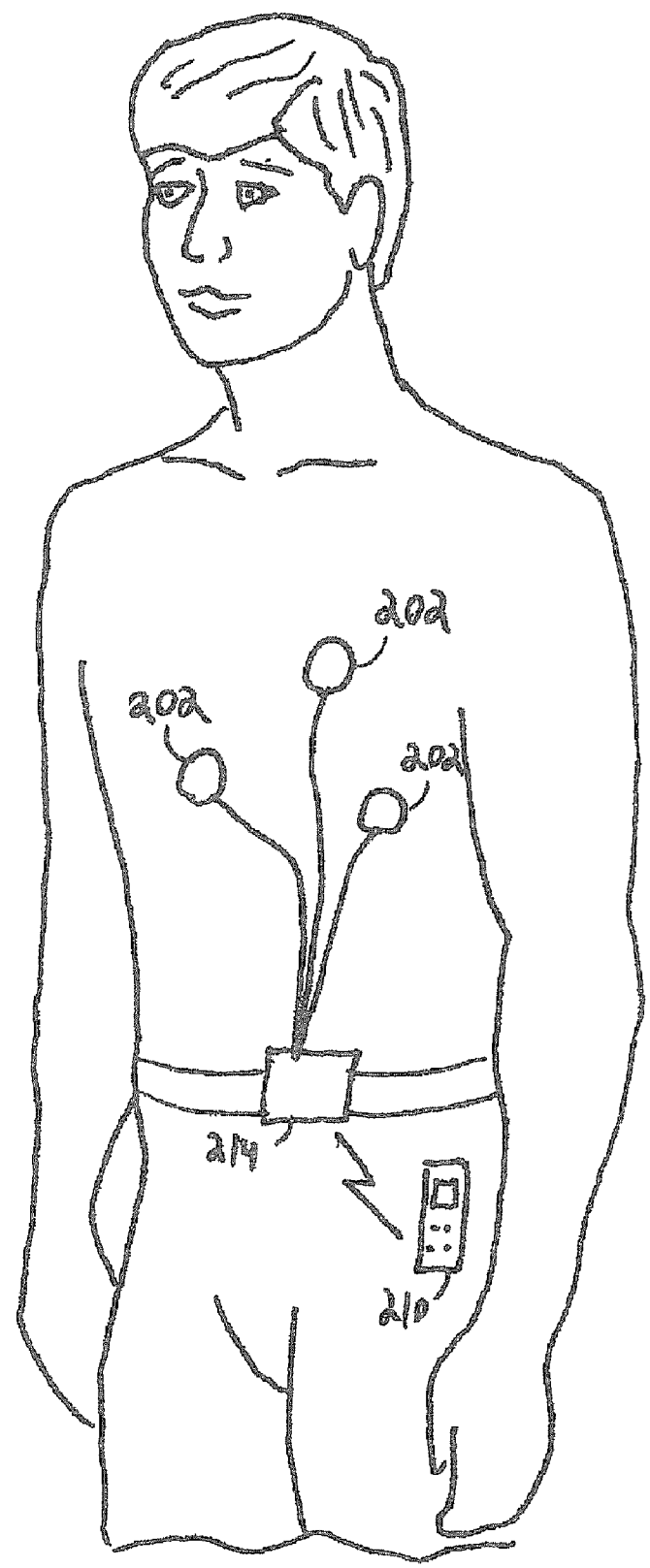

FIG. 6 illustrates another embodiment of the invention in which multiple physiological input devices 202 are connected to an adapter 214 that in turn may generate a multiplexed signal stream that includes signals from one or more of the multiple physiological input devices 202. The adapter 214 conveniently includes one or more analog to digital converters, buffers and a short-range transmitter 206. According to another embodiment of the invention the adapter 214 includes an interface, instead of the short-range transmitter, that is connected to a wire that in turn is connected to cellular phone 210.

According to an embodiment of the invention the adaptor 214 can include a medical sub-system that facilitates the connection of multiple physiological input devices 202 of various types. Such a medical sub-system is described, for example, in U.S. Pat. No. 6,366,871 titled "Personal ambulatory cellular health monitor for mobile patient" of Geva, which incorporated herein by reference.

Figure 7:
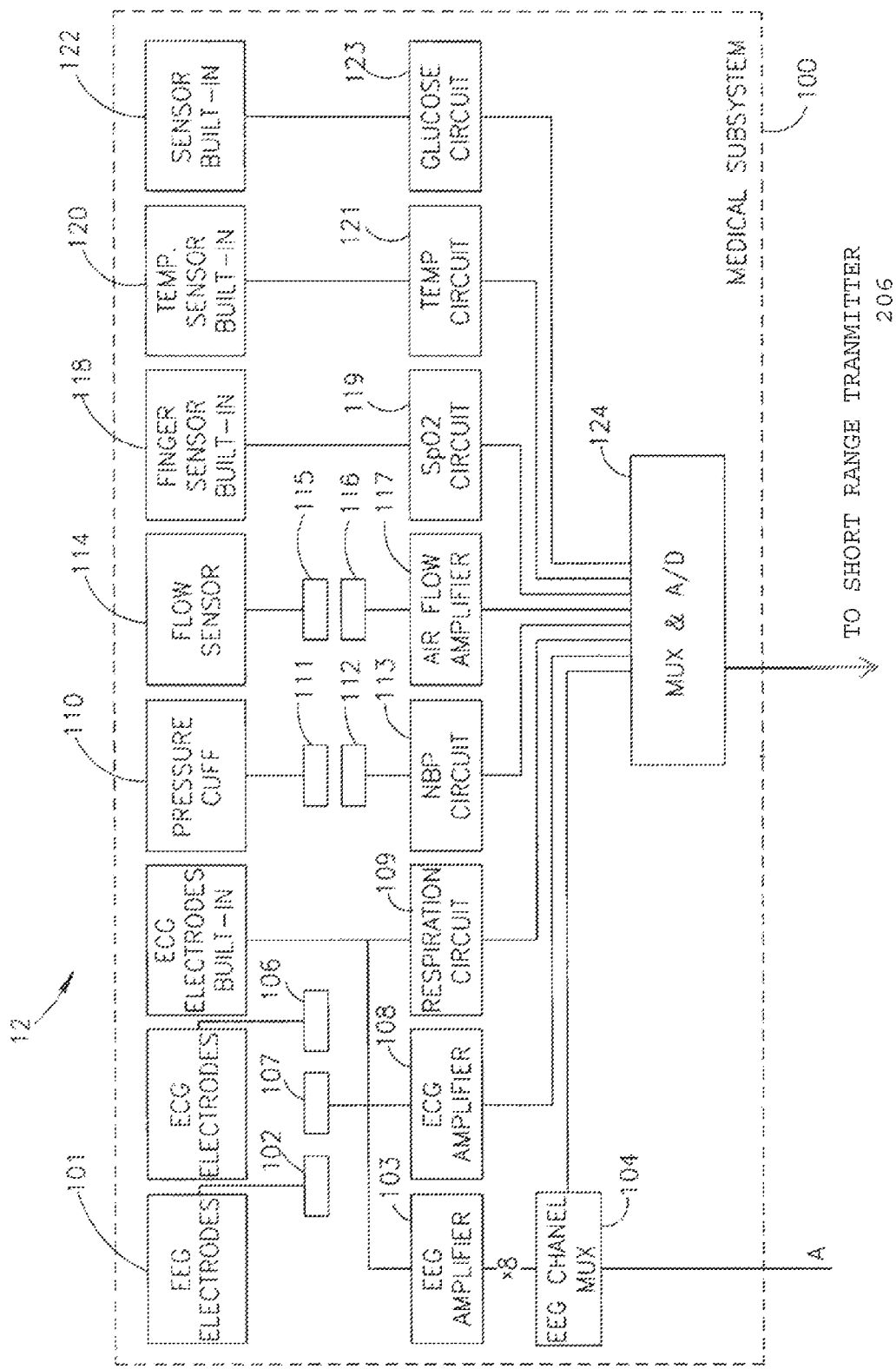
FIG. 7 is a schematic illustration of a medical sub-system.

FIG. 7 illustrates a medical sub-system 100 that includes a multiplexing and analog to digital converter 124 that is connected to multiple analog components such as EEG amplifier 103, ECG amplifier, respiration circuit 109, NBP circuit 113, air flow amplifier 117, Sp02 circuit 119, temperature circuit 121 and glucose circuit 123 that in turn are connected to various sensors such as EEG electrodes 101, ECG electrodes 105, a pressure cuff 110 for measuring NIBP, and an air flow sensor 114 for measuring spirometry, finger sensor 118, temperature sensor 120 and glucose sensor 122. The sensors can be connected directly to the analog circuits or via various connectors or plugs, such as plugs 102, 106, 107, 115, as well as via EEG multiplexer 104. Some of the plugs, such as plug 107, can be used for connecting a first sensor or another sensor, and the connector includes circuitry for determining which sensor is actually connected to the plug.

According to various embodiments of the invention hardware components, such as adaptor 214, physiological input device 202, and alternatively or additionally, short-range transmitter 206 that are connected to the cellular phone by a wire, the cellular phone 210 can be utilized for supplying energy to the wired components. For example, the battery of the cellular phone can be connected, via a wire and/or a connector such as system connector 56 of FIG. 1.

Figure 8:
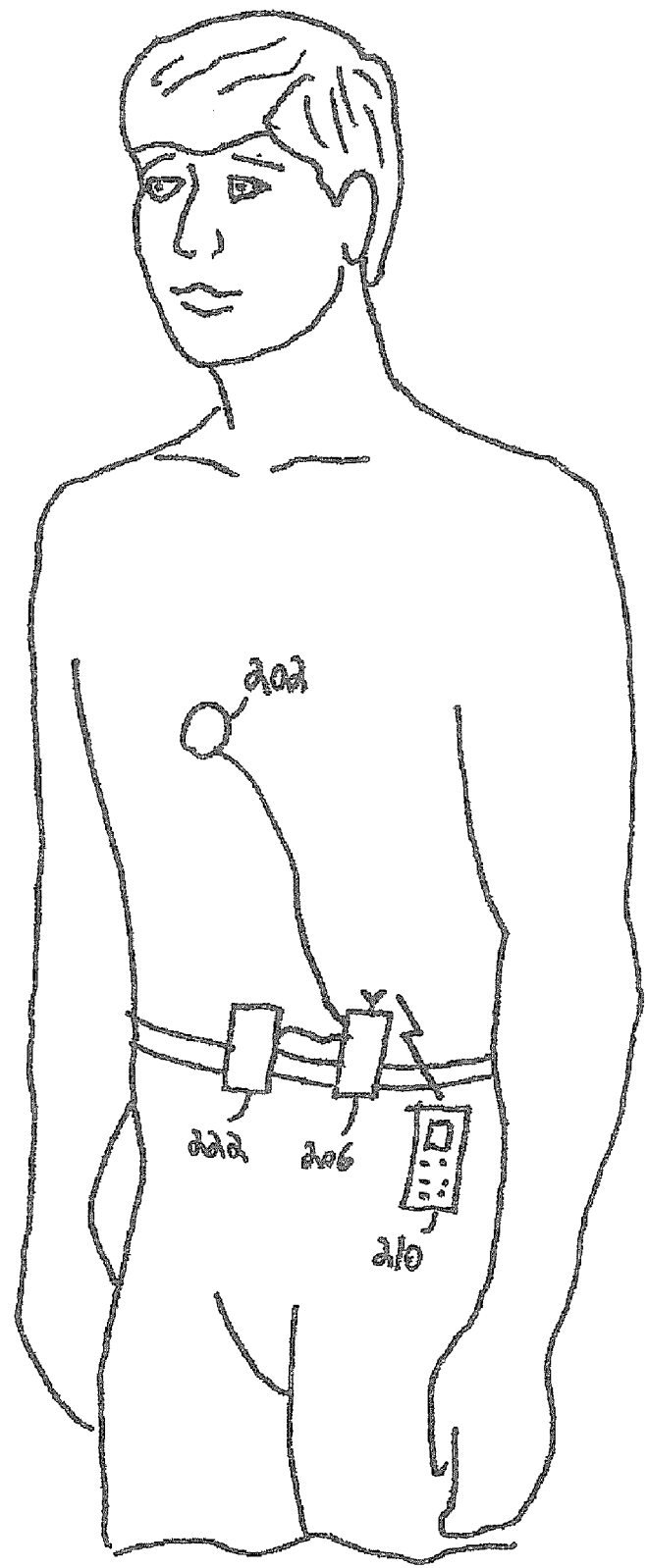

FIG. 8 illustrates another embodiment of the invention in which the person 200 carries one or more physiological data input devices, such as device 202, as well as a personal location subsystem 222 capable of determining a location of the person 200. Thus, location information is also sent to the cellular phone 210 and then long-range transmitted to a remote station (not shown).

The personal location subsystem 222 determines the location of person 200. It usually includes known location determination circuitry such as GPS components including a GPS receiver and a filter that is tuned to a known GPS frequency for CPS satellite communication via a built-in antenna. The personal location subsystem 222 conveniently receives a pseudo range (PR) and pseudo range dot (PRD) from GPS satellites in communication range. The GPS receiver preferably operates in aided mode enabling "snapshot" operation as is known in GPS systems. The position of person 200 and velocity data is conveniently transmitted via a short-range transmitter 206 and to cellular phone 210.

The location of person 200 can be transmitted in predetermined events (Such as location, Distance, Velocity and such as system initialization) or automatically.

Figure 9:
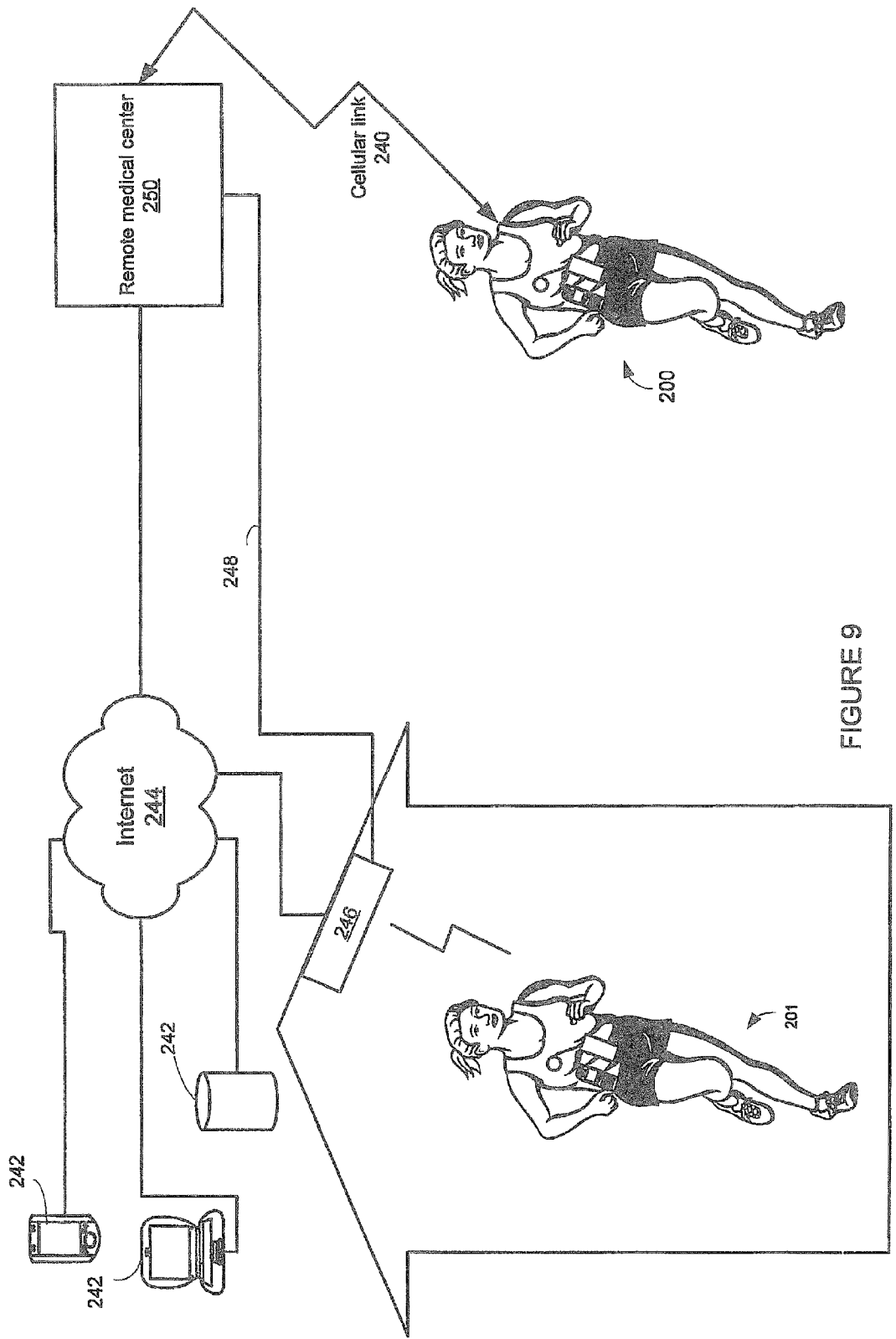
FIG. 9 illustrates a medical center as well as devices for gathering, processing and transmitting physiological data, according to an embodiment of the invention.

Reference is now made to FIG. 9 which is a simplified block diagram illustrating end-to-end communication between a physiological data input devices 202 worn by two persons 200 and 201 and between a remote medical center 230, according to an embodiment of the invention.

The physiological data input device 202 worn by the first person 200 is connected by wire 204 to a short-range transmitter 206. The short-range transmitter 206 transmitted physiological data to cellular phone 210 where the data is processed. The cellular phone 210 is capable of determining whether to transmit the processed physiological data, to transmit a portion of the data or not to transmit it at all.

The cellular phone 210 is connected over a cellular network that is represented by wireless link 240 or via another network such as Internet 244 to a remote medial center 250. The remote medical station 250 can be connected to various databases and accessories 242 via another network such as the Internet 244.

The second person 201 also wears a physiological data input device 202 that is connected by wire 204 to a short-range transmitter 206 that in turn transmits physiological data towards short-range receivers 246 that are capable of transmitting the data to the remote medical center 250 via a WLAN, Cable TV, Satellite TV, CCTV, Telephone line, GSM/GPRS, CDMA, TDMA, iTV, Internet and other network represented by link 248. In this scenario the gathered physiological data can be analyzed by the short-range receiver 246 (or more specifically by a processor that is connected to the receiver). In case of the cable TV, CCTV, ITV, Satellite TV and etc the TV device might be the GUI interface device for user.

Various remote medical centers are also known as central medical monitoring stations and are known in the art. Such a center is described at U.S. Pat. No. 6,366,871 titled "Personal ambulatory cellular health monitor for mobile patient" of Geva, which incorporated herein by reference. It is noted that Geva describes a monitor that is capable of vocal communication with the person, and this feature can be implemented by using the cellular phone 210.

The physiological data input devices 202 and the cellular phone 210 can operate in various modes that include: (i) Event recording activated by the person, either at the person initiative, a third party (such as a clinician) initiative, or pursuant to an alarm, where the person performs one or more tests and transmits processed physiological data to the remote medical center 230. In this mode the remote medical center 230 may be contacted at the beginning of the event for transmission of processed physiological data during the event or at the conclusion of the testing, (ii) Continuous monitoring where physiological data are captured periodically and transmitted to the remote medical center 230. Continuous monitoring may be provided in any of the following ways: Patient-activated event recorder where processed pre-event/event/post-event data is transmitted to the remote medical center 230; Device-activated event recorder where physiological data is detected which fall outside preset parameters; Holter-mode where processed physiological data is transmitted automatically when a buffer of an adaptor or a memory space of the cellular phone allocated for storing the processed (or non-processed) physiological data becomes full; and Holter-mode where processed physiological data is transmitted by a person at any time.

Figure 10:
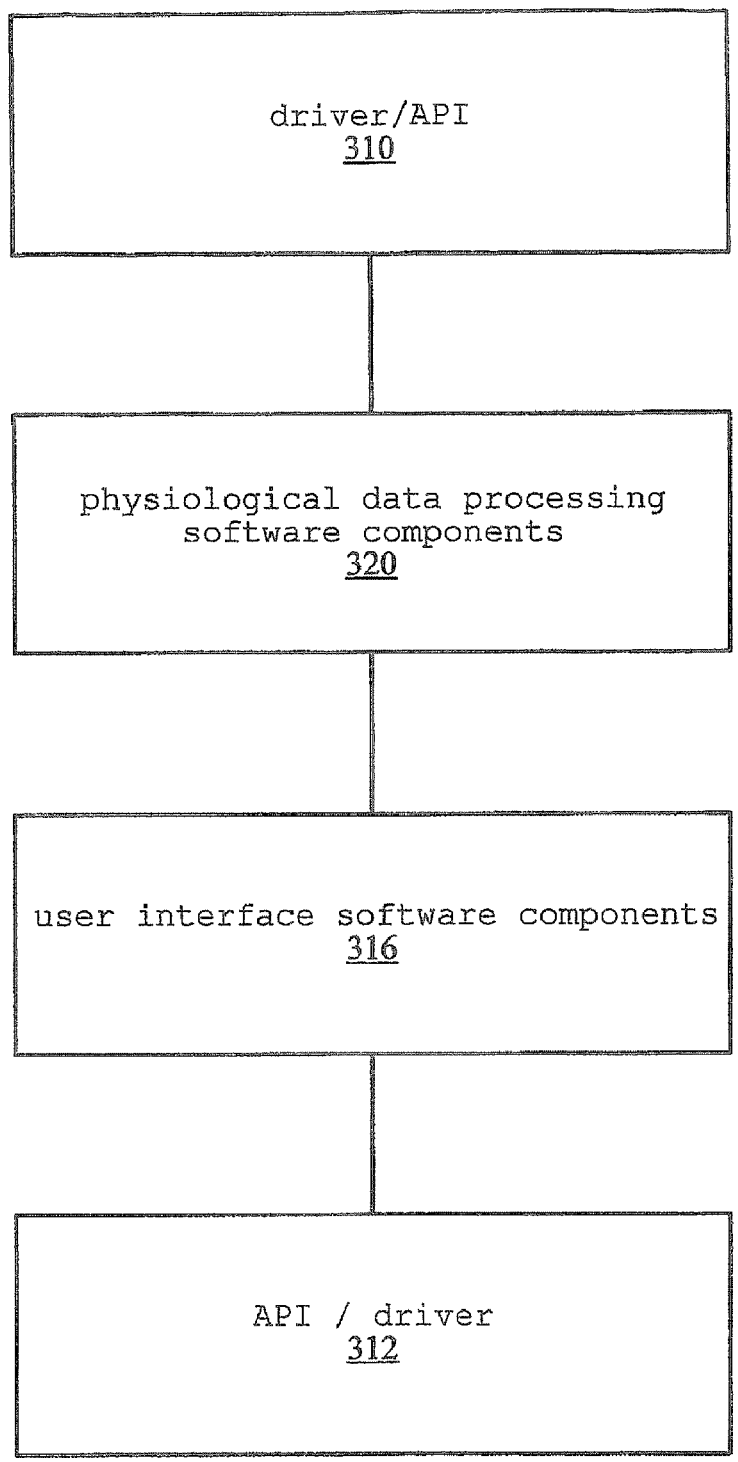
FIG. 10 illustrates a example of the configuration of a health monitoring software that is implemented in the Cellular phone or PDA, according to an embodiment of the invention.

FIG. 10 illustrates a configuration of the health monitoring software 300, according to an embodiment of the invention.

The health monitoring software 300 includes a driver/API 310 between the cellular phone and the wireless network for long-range transmission of processed physiological data, for example in accordance to GPRS, CDMA, GSM and the like. The health monitoring software also includes an API or driver 312 for the short-range or wired data link through which the cellular phone receives the physiological data. The health monitoring software also includes physiological data processing software components 314 as well as user interface software components 316.

It is noted that other software configurations can be utilized. It is also noted that the drivers/API can be a part of the non-medical software components of the cellular phone. For example, a cellular phone that has an embedded short-range receiver includes a short-range communication software module, regardless the presence of the medical application.

The user interface component 316 can apply various known in the art techniques, such as but not limited to a menu based interface in which the person can make various selections between various options that are displayed over the display of the cellular phone. It is also noted that given the advanced multimedia capabilities of modern phones the user interface can also include receiving vocal input and outputting vocal output.

The physiological data processing software component 314 can apply various well-known algorithms for processing the physiological data.

For example, the software can enable the personal health monitor 1 to perform at least one of the following: (i) automatic arrhythmia analysis in different quantization levels (up to 8 bits) in different sampling rates (including 100 Hz), (ii) perform one lead arrhythmia detection in various noise conditions, (iii) perform continuous automatic adaptation to the patient normal heartbeat morphology, (iv) perform continuous real time processing and provide, on request, a summary of the patient heart condition, (v) perform environmental and adaptive noise/movement artifact elimination, (vi) enable the person to adjust the definitions of the pathology sequences detected by the system (for example the number of consecutive PVC heartbeats and the minimum heart rate to define VT) and others.

Figure 11:
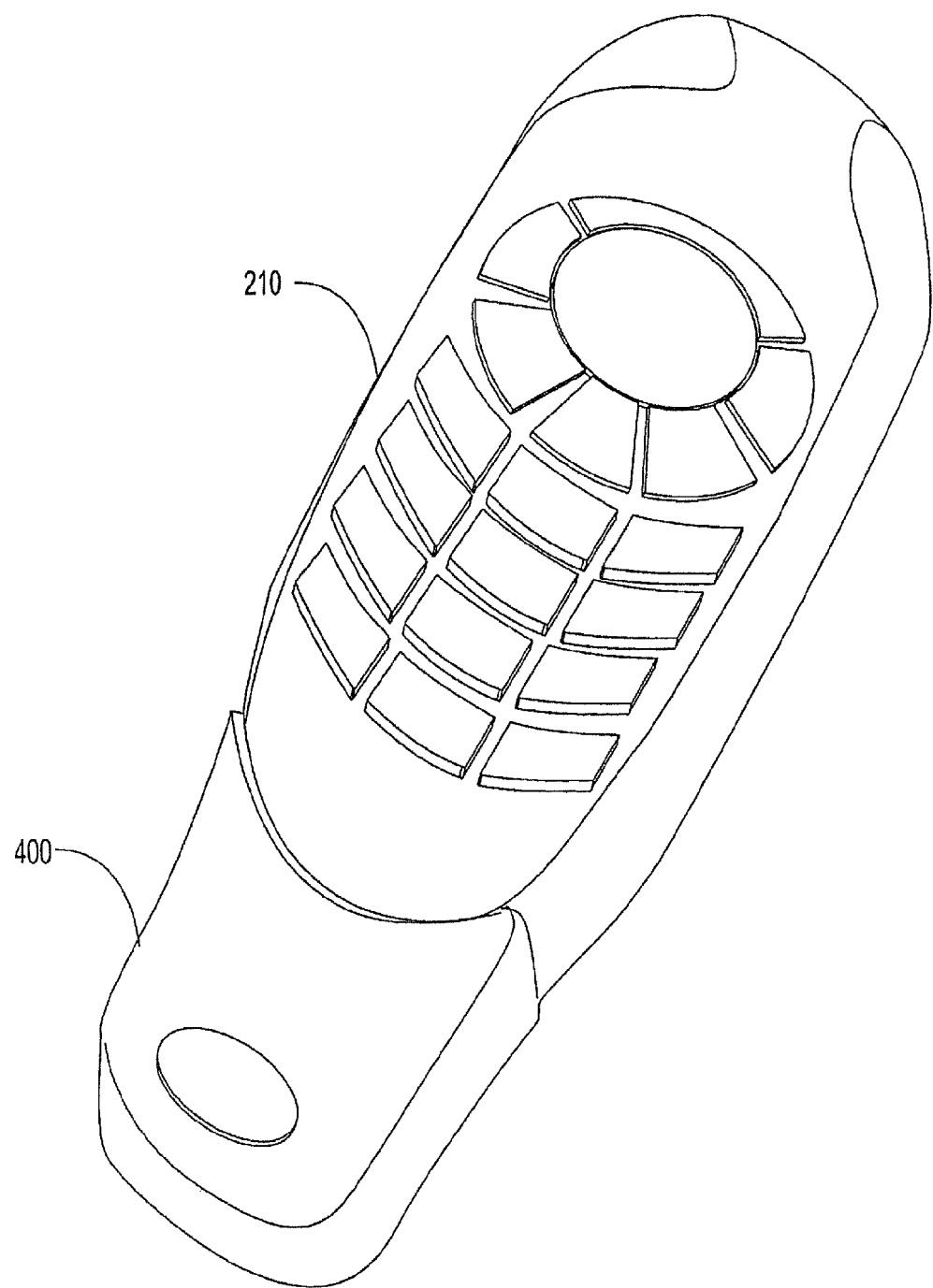
FIG. 11 illustrates a plug-in device that is detachably connected to cellular phone, according to an embodiment of the invention.

The health monitoring software 300 can detect various medical events and determine a medical state of a person. In some operational modes out of the mentioned above modes an occurrence of a medical event can initiate a transmission of processed physiological data and even cause the cellular phone 210 to generate an audio an/or visual alarm message. This health monitoring software 300 can process received physiological data to determine the occurrence of the following: isolated premature ventricular contraction (PVC), isolated premature atrial contraction (PAC), bigeminy, trigeminy, couplet, bradycardia, tachycardia, ventricular tachycardia, supra-ventricular tachycardia. The software can detect a morphology change, perform PR, ST, QRS, QT segmentation, Heart Rate Variability (HRV) analysis and QT Analysis, and the like. According to various embodiments of the invention the health monitoring software 300 can cause the cellular phone to display graphs or other visual representations of the monitored physiological data. According to an embodiment of the invention the cellular phone 210 is capable of retrieving medical information related to the person, and displaying the retrieved medical information. In order to prevent unauthorized use of such a feature the cellular phone can apply various measures such as password protection, biometric measures and the like. FIG. 11 illustrates a plug-in device 400 that is detachably connected to cellular phone 210, according to an embodiment of the invention. The plug-in device can gather one or more type of physiological data, and can include one or more of the previously mentioned sensors, analog circuitry and even can include a multiplexer and analog to digital converter and cable/direct connection and communication to the Cellular Phone that is based on the micro controller. The following scenarios provide example of the interaction between the person and the monitor. For simplicity of explanation we refer to the plug-in device of FIG. 11 but this also applies to the previously mentioned configurations. A sugar level test includes the following stages: the person initialized the test by pressing a certain button, the person inserts a strip in a strip chamber of the plug-in device, the person places a drop of blood on the strip, the plug in sends physiological data reflecting the content of that drop to the cellular phone 210 that in turn processes the gathered physiological data to determine the level of sugar. The person can also view pervious sugar level tests, for example during a time period defined by the person. The cellular phone can display a history trend graph of results with normal level highlighted in a different color. A ECG test can include the following stages: the person presses on a certain button, the person places his fingers on an electrode, the personal physiological monitor retrieves and processes physiological data to determine the stage of the person, a cardiogram is displayed on the monitor of the cellular phone. The person can see the result of previous tests and/or determine whether to save the results of the current test, and the like.

Figure 12:
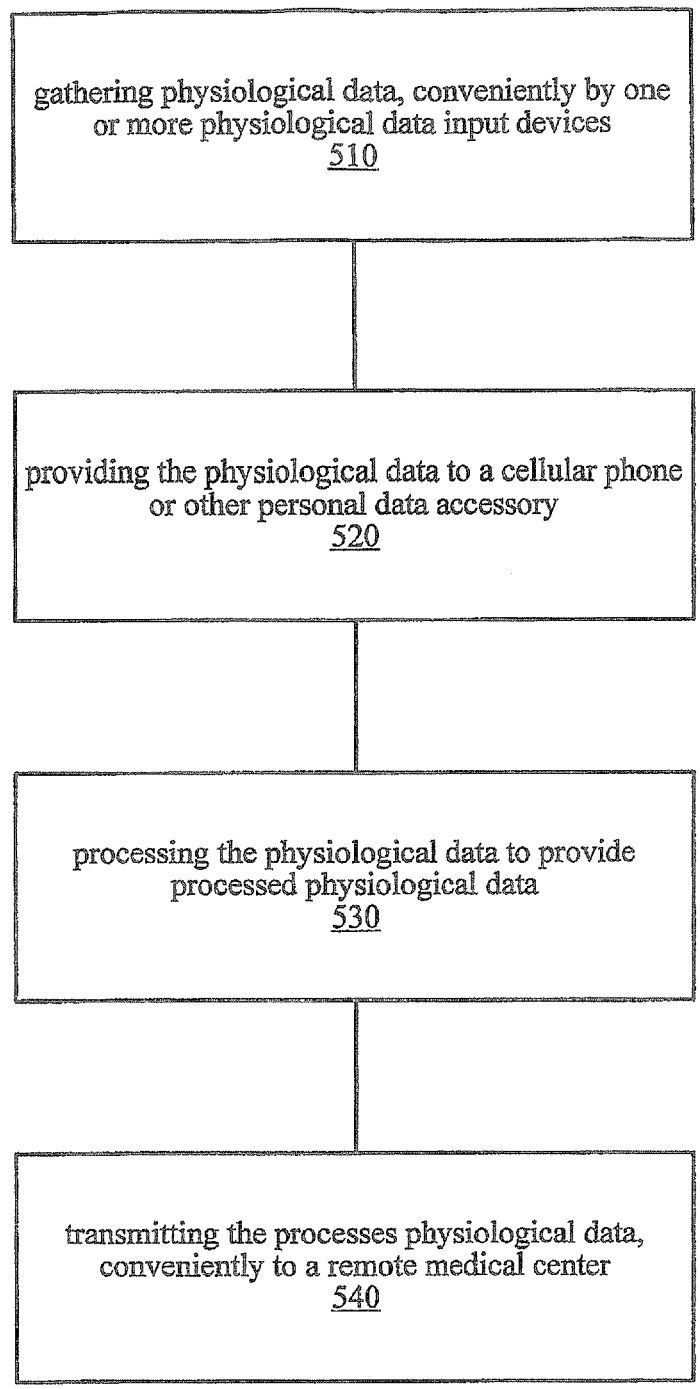
FIG. 12 is a flow chart of method for health monitoring, according to an embodiment of the invention.

FIG. 12 is a flow chart of method 500 for health monitoring, according to an embodiment of the invention.

Method 500 starts by stage 510 of gathering physiological data, conveniently by one or more physiological data input devices. Conveniently, one of the configurations illustrated at FIGS. 3-6, 8 can be used. Data is gathered by one or more physiological data input device.

Stage 510 is followed by stage 520 of providing the physiological data to a cellular phone or other personal data accessory. This stage can include short-range transmission of the physiological data, wire based transmission and the like.

Stage 520 is followed by stage 530 of processing the physiological data to provide processed physiological data. Stage 530 may include applying various well-known algorithms, such as those previously mentioned.

Stage 530 is followed by stage 540 of transmitting the processes physiological data, conveniently to a remote medical center. This stage usually includes long-range transmission of the information.

According to another embodiment of the invention the analyzed physiological data as well as optional information from the personal location can be sent to a center, such as medical center 250 and may be utilized for providing and controlling a diet and/or exercise regime. For example, a person starts to run and begins to transmit location information. This location information along with the timing of its transmission can be used to determine if the person runs, the distance that he runs and even an estimated calorie consumed during this running session. This data can be added to physiological data such as heart rate and fat measurement to provide an indication about the progress of the person in a diet physical fitness regime. The cellular phone 210 can be used to process above mentioned data and display the person indications about scheduled meals, physical exercises, and the like or the above data can be processed in medical center 250 and The cellular phone 210 can be used to send the person indications about scheduled meals, physical exercises, and the like.

It will be appreciated by persons skilled in the art that the present invention is not limited to what has been particularly shown and described hereinabove.

Those skilled in the art will readily appreciate that various modifications and changes may be applied to the preferred embodiments of the invention as hereinbefore exemplified without departing from its scope as defined in and by the appended claims.

Figure 13:
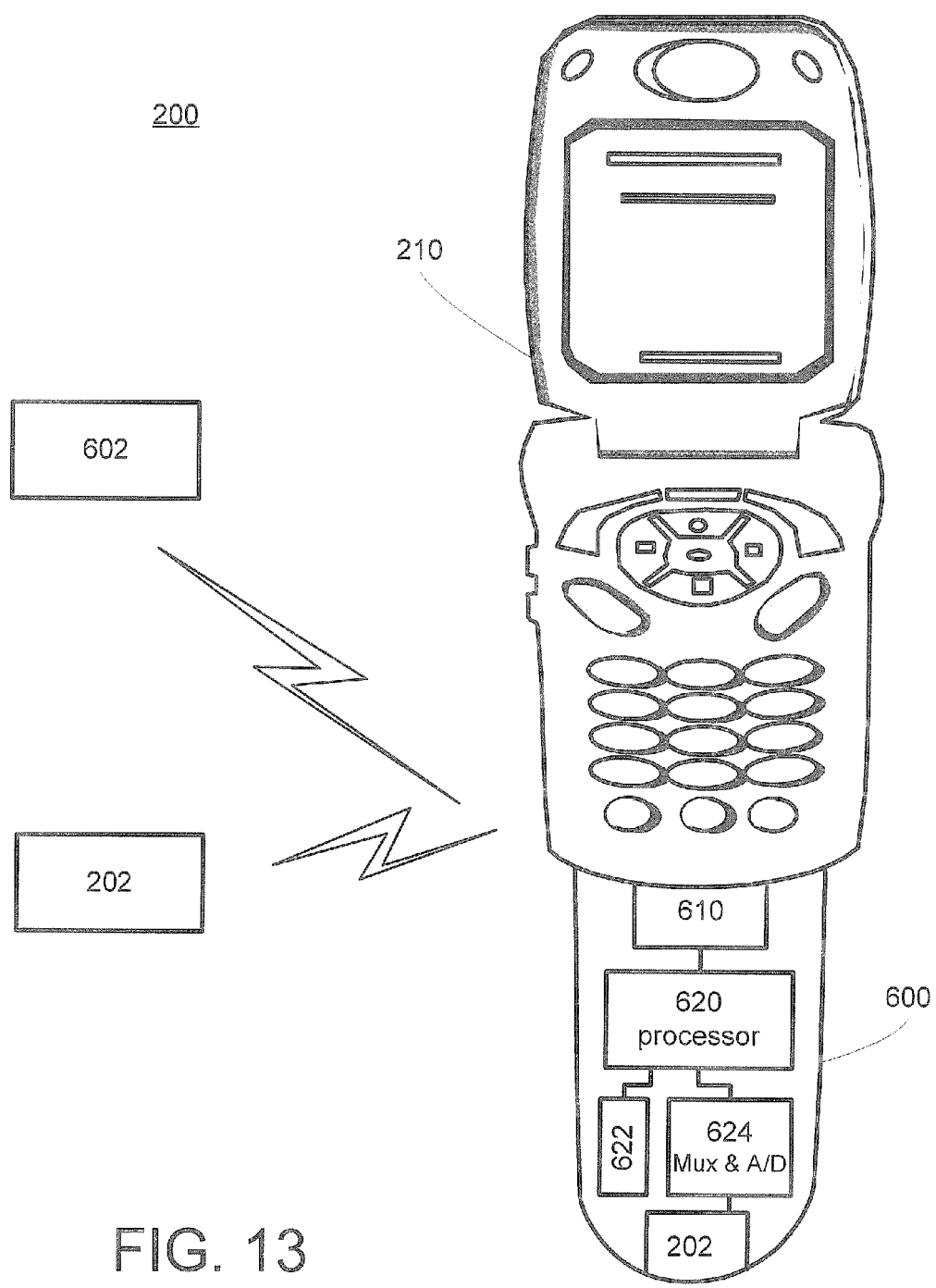
FIG. 13 illustrates a personal health monitor, according to an embodiment of the invention.

FIG. 13 illustrates personal health monitor 200, according to an embodiment of the invention. Personal health monitor 200 includes at least one physiological data input device 202 which is operative to gather physiological data, detachable module 600 that is detachably connected to multi-purpose personal data accessory 210 which is operative to transmit the physiological data to the multi-purpose personal data accessory 210. A communication component 610 of the detachable module transmits the physiological data (either not-processed or at least partly processed) to multi-purpose personal data accessory 210, whereas multi-purpose personal data accessory 210 is adapted to execute health monitoring software such as to enable the multi-purpose personal data accessory to receive the physiological data, process the physiological data to provide processed physiological data and control a long range transmission of the processed physiological data to a remote entity.

It should be noted that detachable module 600 is conveniently detachably attachable to multi-purpose personal data accessory 210 (e.g. a dongle, or via a cable). However, it is also noted that, according to an embodiment of the invention, a module parallel to detachable module 600 and of similar functionalities may communicate with multi-purpose personal data accessory 210 in a wireless manner.

It is noted that at least one physiological data input device 202 may be included within detachable module 600 (e.g. a built-in temperature sensor), and/or at least physiological data input device 202 may be external to detachable module 600 (e.g. an ECG electrode), wherein the physiological data may be transmitted to detachable module either wirelessly or over a wire. Examples of physiological data input devices 202 which may be implemented are offered above, inter alia in relation to medical subsystem 100.

It is also noted that according to some embodiments of the invention, some or all of the functionalities with are disclosed in relation to detachable module 600 and to component thereof (e.g. local processor 620) may be carried out by multi-purpose personal data accessory 210 and/or by components thereof (e.g. a processor of multi-purpose personal data accessory 210).

According to an embodiment of the invention, physiological data and/or signals which are received from one or more physiological data input devices 202 are amplified and/or converted from analog to digital by A/D unit 624 of detachable module 600 (which may also multiplex signals received from multiple physiological data input devices 202, according to an embodiment of the invention). Is it also noted that physiological data of some physiological data input devices 202 may be transmitted, according to an embodiment of the invention, directly to multi-purpose personal data accessory 210 (e.g. via Bluetooth protocol), but according to the herein disclosed embodiments of the invention, detachable module 600 receives physiological data from some or all of the physiological data input devices 202.

As aforementioned, system 200 may include more than one physiological data input devices 202. According to an embodiment of the invention, system 200 further includes at least one controllable sensor (which may either be a second physiological data input device 202 or an environmental sensor 602 which is operative to gather environmental data), wherein the multi-purpose personal data accessory 210 is adapted to execute the health monitoring software such as to enable the multi-purpose personal data accessory 210 to process physiological data that is received from the physiological data input device 202, and to activate the controllable sensor in response to a result of the processing.

Such an implementation may be efficient in several ways, as it may save, for example, power (when the controllable sensor is not operative), bandwidth (when physiological data of the controllable sensor is not received and/or transmitted), computational power (of the physiological data of the second physiological data input device 202), and so forth. It is also noted that detachable module 600 may, according to an embodiment of the invention, receive physiological data from several physiological data input devices 202, and to determine (usually after processing this data) not to transmit physiological data of one or more of the physiological data input devices 202 or external sensor 602 (e.g. due to bandwidth constrains).

As is discussed below in more details, according to an embodiment of the invention, detachable module 600 includes a local processor 620 that is configured to process the physiological data received from physiological data input devices 202, and according to an embodiment of the invention, local processor 620 processes physiological data that is received from the physiological data input device 202, and to activate the controllable sensor in response to a result of the processing.

By way of an example, according to an embodiment of the invention, the health monitoring software enables the multi-purpose personal data accessory 210 (or the local processor 620) to process physiological data that is received from a pulse sensor, and if the pulse rate is detected to increase, to select to activate an environmental temperature sensor, so as to determine if the increased heart rate is a result of external conditions or of a health event.

According to an embodiment of the invention, system 200 includes a second sensor (that is either a physiological data input device 202 or an environmental sensor 602), wherein the multi-purpose personal data accessory 210 is adapted to execute the health monitoring software such as to enable the multi-purpose personal data accessory 210 to process physiological data that is received from the physiological data input device 202 (potentially in addition information that is received from the second sensor) and to control the long range transmission of the processed physiological data to the remote entity to selectively transmit processed physiological data of the second sensor in response to a result of the processing.

According to an embodiment of the invention, system 200 includes a location determination circuitry for providing location information to the multi-purpose personal data accessory 210 and/or to local processor 620, wherein the multi-purpose personal data accessory 210 (or local processor 620) is adapted to execute its health monitoring software such as to enable the multi-purpose personal data accessory 210 (or the local processor 620) to process the location information to determine an activity status of a user of system 200, and to process the physiological data that is received from the physiological data input device 202 in response to the activity status.

It is noted that according to different embodiments of the invention, the location determination circuitry may be external to detachable module 600 (e.g. personal location subsystem 222) or included in which (e.g. internal location subsystem 622). As aforementioned, the location determination circuitry may include GPS circuitry for gathering GPS location information.

According to different embodiments of the invention, the location determination circuitry is configured to provide immediate local information with a higher resolution that is possible with GPS circuitry, and/or in situations when GPS information is not available (e.g. no satellite coverage). Such information may include for example acceleration information, direction, and so forth.

According to an embodiment of the invention, the location determination circuitry is configured to provide location information from an accelerometer of the system (either internal or external to detachable module 600). According to an embodiment of the invention, the location determination circuitry is configured to provide location information from a pedometer of the system (either internal or external to detachable module 600). According to an embodiment of the invention, the location determination circuitry is configured to provide location information from a magnetic compass of the system (either internal or external to detachable module 600).

Thus, for example, if a health indicative condition is detected by physiological data received from at least one physiological data input device 202 (e.g. pulse rate increasing), data from the location determination using may be used to determine if there is a reason which count for the health indicative condition (e.g. if the user is running, the heart rate suppose to increase).

According to an embodiment of the invention, the multi-purpose personal data accessory 210 (or the local processor 620) is adapted to execute the health monitoring software such as to enable the multi-purpose personal data accessory 210 (or the local processor 620) to process the location information to selectively provide a falling alert, indicative of a falling of the user (which may be transmitted to an emergency medical service system; for example).

According to an embodiment of the invention, system 200 includes one or more environmental sensors 602 operative to gather environmental data, wherein the multi-purpose personal data accessory 210 (or the local processor 620) is adapted to execute the health monitoring software such as to enable the multi-purpose personal data accessory 210 (or the local processor 620) to process the physiological data that is received from the physiological data input device 202 in response to the environmental data.

Exemplary types of such environmental sensors 601 are temperature sensor, humidity sensor, pollution detectors (especially gaseous pollution detectors), and so forth.

The environmental sensor may be used to explain a possible health indicative condition (e.g. high pulse resulting from hot environment), and may also be used for recommending a user to move to another environment (e.g. a cooler environment or a less humid one), either in relation to a detected health indicative condition, or generally (e.g. to stay away from a polluted area). It is noted that such recommendation may be general, and may also be responsive to a medical condition definitions of the specific user (e.g. allergies, heart condition, etc.).

As aforementioned, according to an embodiment of the invention, detachable module 600 includes a processor 620 (also referred to as local processor). According to an embodiment of the invention, processor 620 is adapted to execute a second health monitoring software such as to enable processor 620 to receive the physiological data, process the physiological data to provide locally processed physiological data and to selectively provide alerts in response to the locally processed physiological data.

It is noted that usually, processing capabilities and/or interfacing capabilities of processor 620 (and/or other components of detachable module) would be lesser than those of multi-purpose personal data accessory 210. For example, usually detachable module 600 would have no display at all, or a display that is lesser than a high resolution video capable display which is available in many commercial cellular phones and PDAs. Therefore, it is noted that while the second health monitoring software may be similar to the health monitoring software that is run by multi-purpose personal data accessory 210, it may also have lesser capabilities (e.g. performing only some of the analyzing).

Using the capabilities of the detachable module 600 may prove beneficial in different scenarios, e.g. when the multi-purpose personal data accessory 210 is not available (e.g. forgotten, have no battery, etc.).

According to an embodiment of the invention, processor 620 of detachable module 600 is further adapted to control a long range transmission of the locally processed physiological data to the remote entity by a cellular modem that is connected to the detachable module 600 and which is external to the multi-purpose personal data accessory. It is noted that the cellular modem may be internal to detachable module 600 (not shown), or external to it (such as commercial cellular modems which are currently available at market). Alternatively, other types of modems or general communication components may be used for the long range transmission.

According to an embodiment of the invention, detachable module 600 includes a storage compartment (not shown) for storing medication, wherein system 200 is further configured to provide medication regime timing alerts (usually using a proper health monitoring software).

According to an embodiment of the invention, system 200 is capable of keeping track of medications taken by the user (e.g. by user approval of taking prescribed medications, or otherwise indicating medications taken, or by detecting remaining medications in the storage compartment), and to create alerts in response to medications not taken and/or to include this information in physiological data transmissions.

Conveniently, detachable module 600 is modular, in the sense that external sensors or other units (such as battery, modem, etc.) may be connected to it, to expand its capabilities.

According to an embodiment of the invention, detachable module includes a display (not shown) for providing visual indications upon need. According to an embodiment of the invention, the display is a textual display capable of displaying short text messages such as "low battery", "ECG electrode disconnected", "impedance problems" etc.

According to an embodiment of the invention, detachable module 600 includes an at least one internal power supply (not shown), which may also be used, according to an embodiment of the invention, for supplying power to external components such as sensors. According to an embodiment of the invention, detachable module 600 is capable of transmitting power from multi-purpose personal data accessory 210 to peripheral components. According to an embodiment of the invention, detachable module 600 (or system 200 in general) includes a recharge module (e.g. dynamical/photoelectric/thermal one).

It is noted that according to an embodiment of the invention, a processor of system 200 is capable of managing power consumption, e.g. by activating only some of the sensors in a low battery mode.

According to an embodiment of the invention, detachable module 600 includes an internal memory unit.

According to an embodiment of the invention, detachable module 600 includes at least one service connector (e.g. USB, RS232, RF, ZigBee, Wi-Fi, Wimax, etc.).

According to an embodiment of the invention, system 200 is adapted to enable a video conference between the user and a remote entity (e.g. a physician in a remote medical facility), and/or to display video media such as emergency conditions handling tutorials etc.

According to an embodiment of the invention, detachable module 600 includes a speaker (not shown) for providing audio alerts and/or information.

According to an embodiment of the invention, detachable module 600 includes a vibrator (not shown) for providing sensual alerts.

FIG. 14 illustrates method 900 for health monitoring, according to an embodiment of the invention. It is noted that conveniently, method 900 is carried out by system 200, and different embodiments of system 200 may be implemented by embodiments of method 900, even if parallel stages are not explicitly elaborated.

Method 900 starts with stage 910 of gathering physiological data by a physiological data input device.

Stage 910 is followed by stage 920 of transmitting the physiological data to the multi-purpose personal data accessory by a detachable module that is detachably connected to the multi-purpose personal data accessory;

Stage 920 is followed by stage 930 of executing health monitoring software by the multi-purpose personal data accessory, to process the physiological data to provide processed physiological data.

Stage 930 is followed by stage 940 of transmitting the processed physiological data to a remote entity.

According to an embodiment of the invention, the processing of the physiological data is followed by stage 941 of controlling a transmission of the processed physiological data to the remote entity to selectively transmit processed physiological data of a sensor other than the physiological data input device in response to a result of the processing. It is noted that the sensor may be another physiological data input device, an environmental sensor, or other sensor or detector, according to an embodiment of the invention.

According to an embodiment of the invention, stage 930 may be followed by stage 970 of activating a controllable sensor in response to a result of the processing, wherein information gathered by the controllable sensor may be processed together with physiological data gather by the physiological data input device to provide extended processed physiological data.

According to an embodiment of the invention, method 900 further includes stage 950 of providing location information by a location determination circuitry, and stage 931 of processing the location information to determine an activity status of a user, wherein the processing of the physiological data (of stage 930) is responsive to the activity status. It is noted that the processing of the physiological data may also be otherwise responsive to location information (e.g. it may be responsive to a distance from a medical institute).

It is noted that, according to an embodiment of the invention, the providing of the location information includes providing location information gathered by an accelerometer of the system.

It is noted that according to an embodiment of the invention, the processing of the location information includes processing the location information to selectively provide a falling alert (denoted 932).

According to an embodiment of the invention, method 900 includes stage 960 of gathering environmental data by an environmental sensor, wherein the processing of the physiological data includes processing the physiological data in response to the environmental data (denoted 933).

It is noted that in some situations (e.g. when processing by the multi-purpose personal data accessory is not available), the gathering of the physiological data may be followed by stage 980 of executing a second health monitoring software by a processor of the detachable module, whereas the processor processes the physiological data to provide locally processed physiological data, which is followed by stage 990 of selectively providing alerts, by the processor, in response to the locally processed physiological data. It is noted that an initial processing may be carried out by the processor of the detachable module, and that the partially processed physiological data (or part of which) may be transmitted to the multi-purpose personal data accessory for further processing and handling.

According to an embodiment of the invention, method 900 includes stage 9100 of controlling by the processor of the detachable module a long range transmission of the locally processed physiological data to the remote entity by a cellular modem that is connected to the processor and which is external to the multi-purpose personal data accessory.

According to an embodiment of the invention, method 900 further includes stage 9110 of providing medication regime timing alerts for medications that are stored in a storage compartment of the detachable module.

According to an aspect of the invention, a computer program product is disclosed (which may be a computer readable code that is stored on a computer readable medium), the computer program product includes instructions that when carried out by at least one processor of a multi-purpose personal data accessory, causes the multi-purpose personal data accessory to execute the following processes: (a) receiving physiological data that was gathered by a (e.g. directly from the physiological data input device, or from a detachable module that is detachably attached to the multi-purpose personal data accessory); (b) executing health monitoring software to process the physiological data to provide processed physiological data; and (c) transmitting the processed physiological data to a remote entity.

According to an embodiment of the invention, the computer program product further includes instructions for activating a controllable sensor in response to a result of the processing.

According to an embodiment of the invention, the computer program product further includes instructions for controlling a transmission of the processed physiological data to the remote entity to selectively transmit processed physiological data of a sensor other than the physiological data input device in response to a result of the processing.

According to an embodiment of the invention, the computer program product further includes instructions for receiving location information gathered by a location determination circuitry, processing the location information to determine an activity status of a user, and processing of the physiological data is responsive to the activity status.

According to an embodiment of the invention, the computer program product further includes instructions for processing the location information to selectively provide a falling alert.

According to an embodiment of the invention, the computer program product further includes instructions for receiving environmental data gathered by an environmental sensor, and processing of the physiological data in response to the environmental data.

According to an embodiment of the invention, the computer program product further includes instructions for processing partly pre-processed information that was processed by a processor of a detachable module detachably connected to the multi-purpose personal data accessory in response to the physiological data.

According to an embodiment of the invention, the computer program product further includes instructions for providing medication regime timing alerts for medications that are stored in a storage compartment of the detachable module.

While certain features of the invention have been illustrated and described herein, many modifications, substitutions, changes, and equivalents will now occur to those of ordinary skill in the art. It is, therefore, to be understood that the appended claims are intended to cover all such modifications and changes as fall within the true spirit of the invention.

What is claimed is:

1. A personal health monitor, comprising:
   a physiological data input device operative to gather physiological data;
   a detachable module that is detachably coupled to a multi-purpose personal data accessory, operative to transmit the physiological data to the multi-purpose personal data accessory; and
   the multi-purpose personal data accessory, whereas the multi-purpose personal data accessory is adapted to execute health monitoring software such as to enable the multi-purpose personal data accessory to receive the physiological data, process the physiological data to provide processed physiological data and control a long range transmission of the processed physiological data to a remote entity.

2. The system according to claim 1, further comprising a controllable sensor, wherein the multi-purpose personal data accessory is adapted to execute the health monitoring software such as to enable the multi-purpose personal data accessory to process physiological data that is received from the physiological data input device and to activate the controllable sensor in response to a result of the processing.

3. The system according to claim 1, further comprising a second sensor, wherein the multi-purpose personal data accessory is adapted to execute the health monitoring software such as to enable the multi-purpose personal data accessory to process physiological data that is received from the physiological data input device and to control the long range transmission of the processed physiological data to the remote entity to selectively transmit processed physiological data of the second sensor in response to a result of the processing.

4. The system according to claim 1, further comprising a location determination circuitry for providing location information to the multi-purpose personal data accessory, wherein the multi-purpose personal data accessory is adapted to execute the health monitoring software such as to enable the multi-purpose personal data accessory to process the location information to determine an activity status of a user, and to process the physiological data that is received from the physiological data input device in response to the activity status.

5. The system according to claim 4, wherein the location determination circuitry is configured to provide location information from an accelerometer of the system.

6. The system according to claim 4, wherein the multi-purpose personal data accessory is adapted to execute the health monitoring software such as to enable the multi-purpose personal data accessory to process the location information to selectively provide a falling alert.

7. The system according to claim 1, further comprising an environmental sensor operative to gather environmental data, wherein the multi-purpose personal data accessory is adapted to execute the health monitoring software such as to enable the multi-purpose personal data accessory to process the physiological data that is received from the physiological data input device in response to the environmental data.

8. The system according to claim 1, wherein the detachable module includes a processor that is adapted to execute a second health monitoring software such as to enable the processor to receive the physiological data, process the physiological data to provide locally processed physiological data and to selectively provide alerts in response to the locally processed physiological data.

9. The system according to claim 8, wherein the processor of the detachable module is further adapted to control a long range transmission of the locally processed physiological data to the remote entity by a cellular modem that is coupled to the processor and which is external to the multi-purpose personal data accessory.

10. The system according to claim 1, wherein the detachable module comprises a storage compartment for storing medication, wherein the system is further configured to provide medication regime timing alerts.

11. A method for health monitoring, comprising:
    gathering physiological data by a physiological data input device;
    transmitting the physiological data to the multi-purpose personal data accessory by a detachable module that is detachably coupled to the multi-purpose personal data accessory;
    executing health monitoring software by the multi-purpose personal data accessory, to process the physiological data to provide processed physiological data; and
    transmitting the processed physiological data to a remote entity.

12. The method according to claim 11, wherein the processing of the physiological data is followed by activating a controllable sensor in response to a result of the processing.

13. The method according to claim 11, wherein the processing of the physiological data is followed by controlling a transmission of the processed physiological data to the remote entity to selectively transmit processed physiological data of a sensor other than the physiological data input device in response to a result of the processing.

14. The method according to claim 11, further comprising providing location information by a location determination circuitry, processing the location information to determine an activity status of a user, wherein the processing of the physiological data is responsive to the activity status.

15. The method according to claim 14, wherein the providing of the location information comprises providing location information gathered by an accelerometer of the system.

16. The method according to claim 14, wherein the processing of the location information comprises processing the location information to selectively provide a falling alert.

17. The method according to claim 11, further comprising gathering environmental data by an environmental sensor, wherein the processing of the physiological data comprises processing the physiological data in response to the environmental data.

18. The method according to claim 11, comprising executing a second health monitoring software by a processor of the detachable module, whereas the processor processes the physiological data to provide locally processed physiological data; and selectively providing alerts, by the processor, in response to the locally processed physiological data.

19. The method according to claim 18, further comprising controlling by the processor of the detachable module a long range transmission of the locally processed physiological data to the remote entity by a cellular modem that is coupled to the processor and which is external to the multi-purpose personal data accessory.

20. The method according to claim 11, further comprising providing medication regime timing alerts for medications that are stored in a storage compartment of the detachable module.

* * * * *